US011013897B2

(12) United States Patent
Lin et al.

(10) Patent No.: US 11,013,897 B2
(45) Date of Patent: May 25, 2021

(54) APPARATUS FOR BENDING MALLEABLE GUIDE OF SURGICAL INSTRUMENT

(71) Applicant: Acclarent, Inc., Irvine, CA (US)

(72) Inventors: Arthur M. Lin, Fremont, CA (US); Thomas R. Jenkins, Alameda, CA (US)

(73) Assignee: Acclarent, Inc., Irvine, CA (US)

( * ) Notice: Subject to any disclaimer, the term of this patent is extended or adjusted under 35 U.S.C. 154(b) by 78 days.

(21) Appl. No.: 16/158,765

(22) Filed: Oct. 12, 2018

(65) Prior Publication Data

US 2019/0105481 A1 Apr. 11, 2019

Related U.S. Application Data

(62) Division of application No. 14/928,260, filed on Oct. 30, 2015, now Pat. No. 10,137,286.

(51) Int. Cl.
*A61M 29/02* (2006.01)
*A61B 17/24* (2006.01)
*A61B 17/12* (2006.01)
*A61B 17/00* (2006.01)

(52) U.S. Cl.
CPC ....... *A61M 29/02* (2013.01); *A61B 17/12104* (2013.01); *A61B 17/12136* (2013.01);
(Continued)

(58) Field of Classification Search
CPC ......... A61B 17/12; A61B 17/00; A61B 17/24; A61B 17/12022; A61B 17/12145;
(Continued)

(56) References Cited

U.S. PATENT DOCUMENTS 5,634,475 A * 6/1997 Wolvek ........... A61M 25/09041
600/585
6,273,887 B1 * 8/2001 Yamauchi .......... A61B 18/1442
606/48
(Continued)

FOREIGN PATENT DOCUMENTS

| CN | 102271749 A | 12/2011 |
| CN | 104646461 A | 5/2015 |
| WO | WO 2011/140535 A1 | 11/2011 |

OTHER PUBLICATIONS

International Search Report and Written Opinion dated Jan. 4, 2017 for Application No. PCT/US2016/058728, 11 pgs.
(Continued)

*Primary Examiner* — Vi X Nguyen
(74) *Attorney, Agent, or Firm* — Frost Brown Todd LLC

(57) ABSTRACT

An apparatus includes a grounding member and an actuator. The grounding member includes a first grounding feature and a bending channel. The first grounding feature is configured to engage a dilation instrument. The bending channel is configured to receive a malleable member of the dilation instrument. The actuator is pivotably coupled with the grounding member. The actuator has a bearing surface. The bearing surface is configured to cooperate with the bending channel to thereby bend the malleable member of the dilation instrument as the actuator is pivoted relative to the grounding member.

15 Claims, 33 Drawing Sheets

(52) U.S. Cl.
CPC .... *A61B 17/24* (2013.01); *A61B 2017/00946* (2013.01); *A61M 2029/025* (2013.01); *A61M 2209/04* (2013.01)

(58) Field of Classification Search
CPC ........ A61B 17/12104; A61B 17/12136; A61B 2017/00946; A61B 2017/1205; A61M 29/00; A61M 29/02
See application file for complete search history.

(56) References Cited

U.S. PATENT DOCUMENTS

| | | |
|---|---|---|
| 9,155,492 B2 | 10/2015 | Jenkins et al. |
| 9,226,800 B2 | 1/2016 | Burg et al. |
| 9,554,817 B2 | 1/2017 | Goldfarb et al. |
| 10,137,286 B2 | 11/2018 | Lin et al. |
| 2006/0063973 A1 | 3/2006 | Makower et al. |
| 2006/0217706 A1 | 9/2006 | Lau et al. |
| 2010/0030031 A1 | 2/2010 | Goldfarb et al. |
| 2011/0004057 A1 | 1/2011 | Goldfarb et al. |
| 2011/0022172 A1 | 1/2011 | Gonzales et al. |
| 2012/0071857 A1 | 3/2012 | Goldfarb et al. |
| 2014/0074141 A1 | 3/2014 | Johnson et al. |
| 2016/0310714 A1 | 10/2016 | Jenkins et al. |

OTHER PUBLICATIONS

Chinese Office Action dated Apr. 29, 2020 for Application No. 201680062765.5, 13 pages.

\* cited by examiner

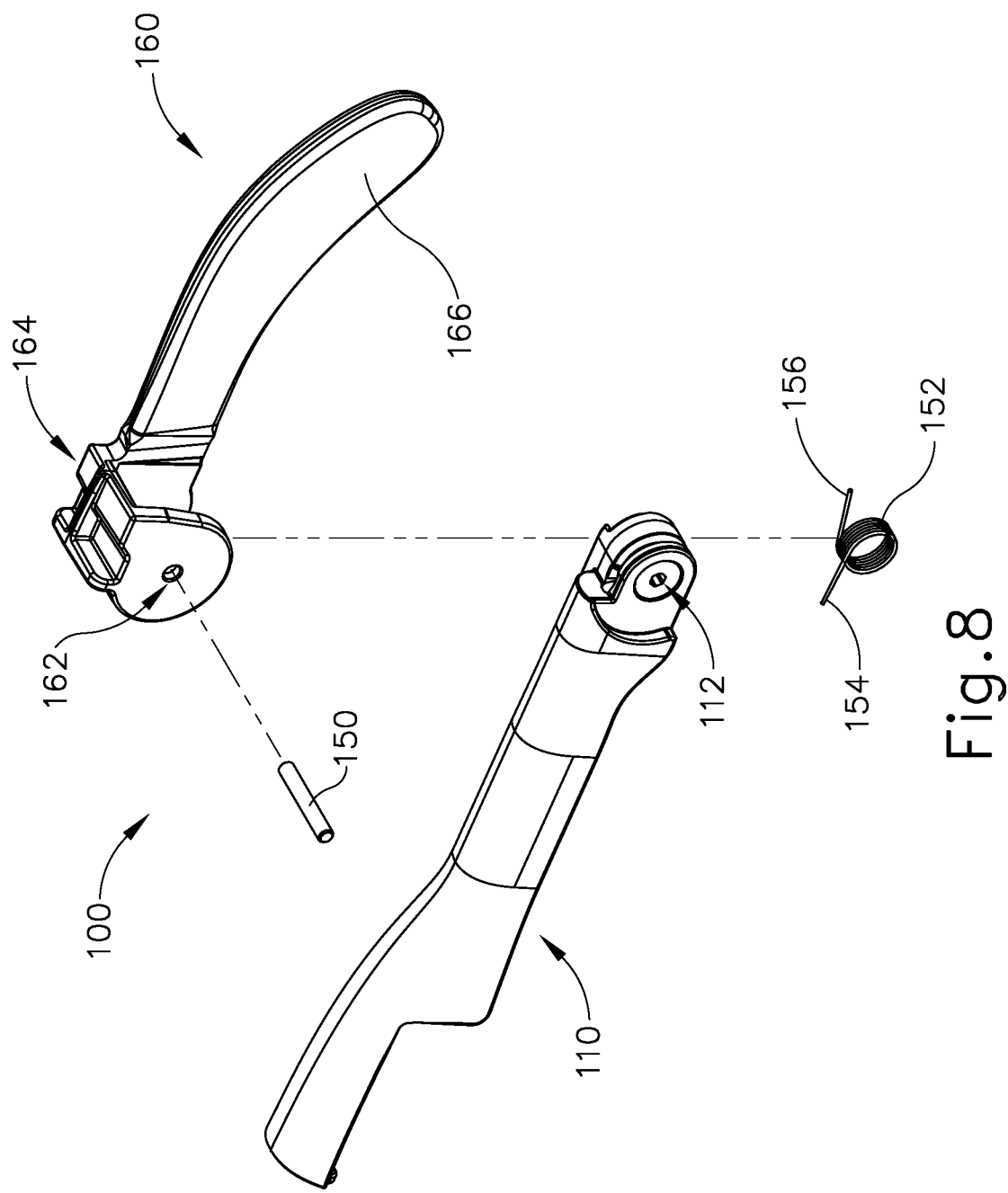

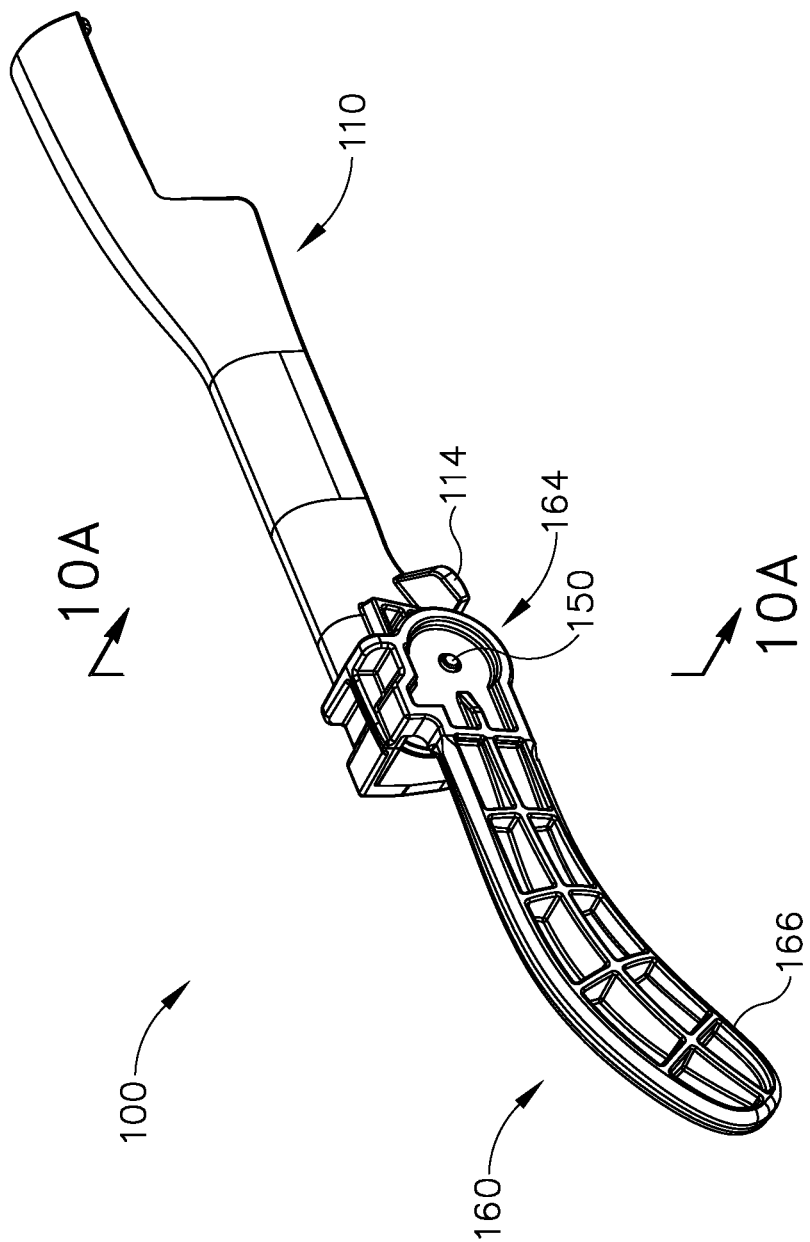

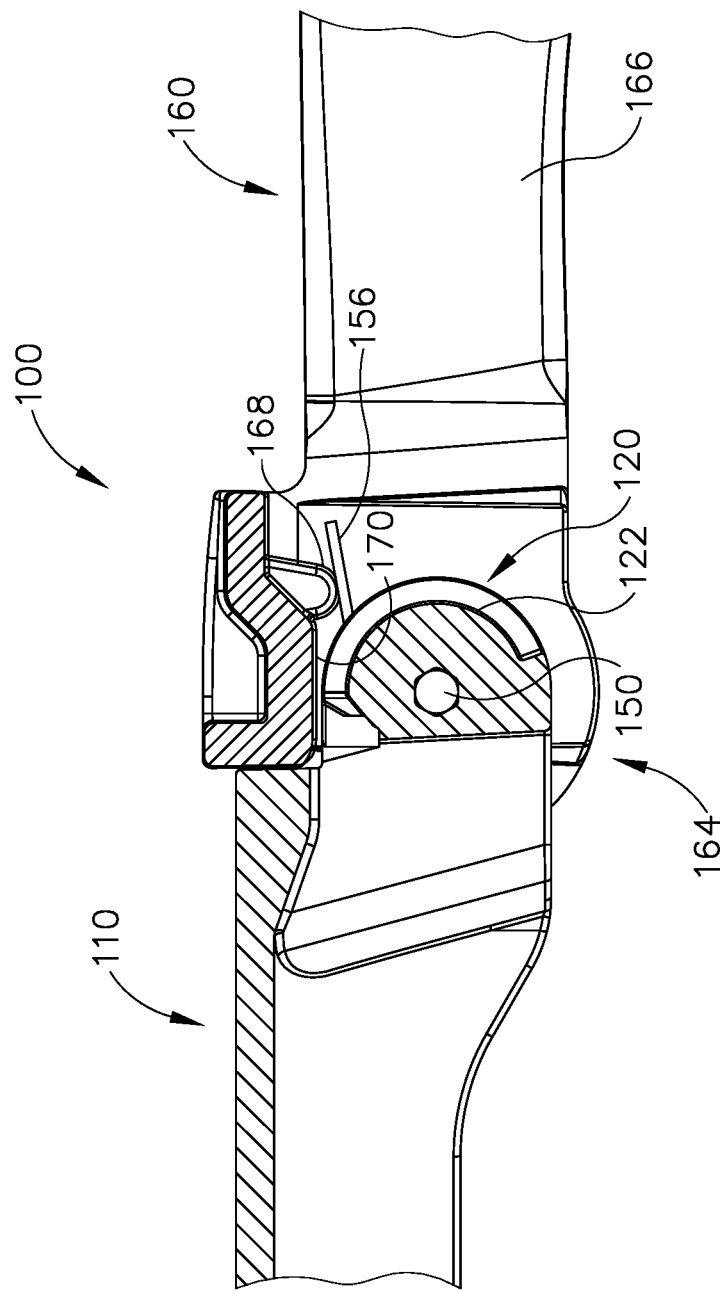

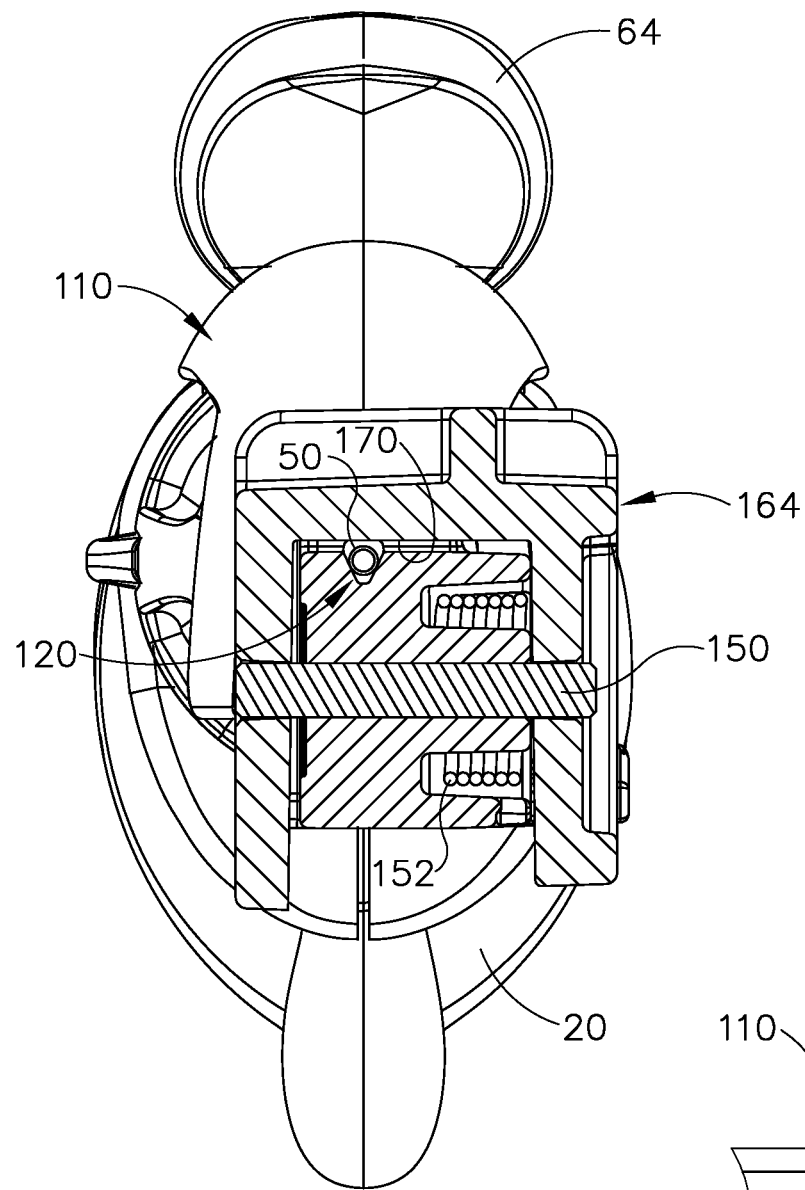
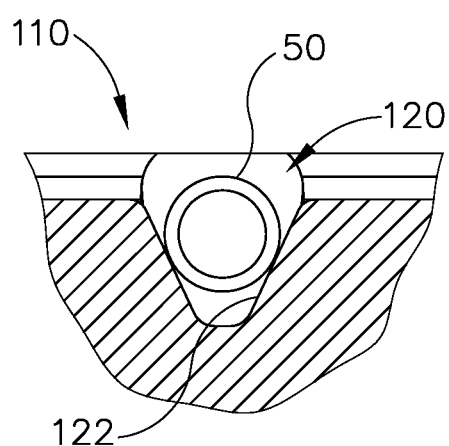
Fig.18
Fig.19

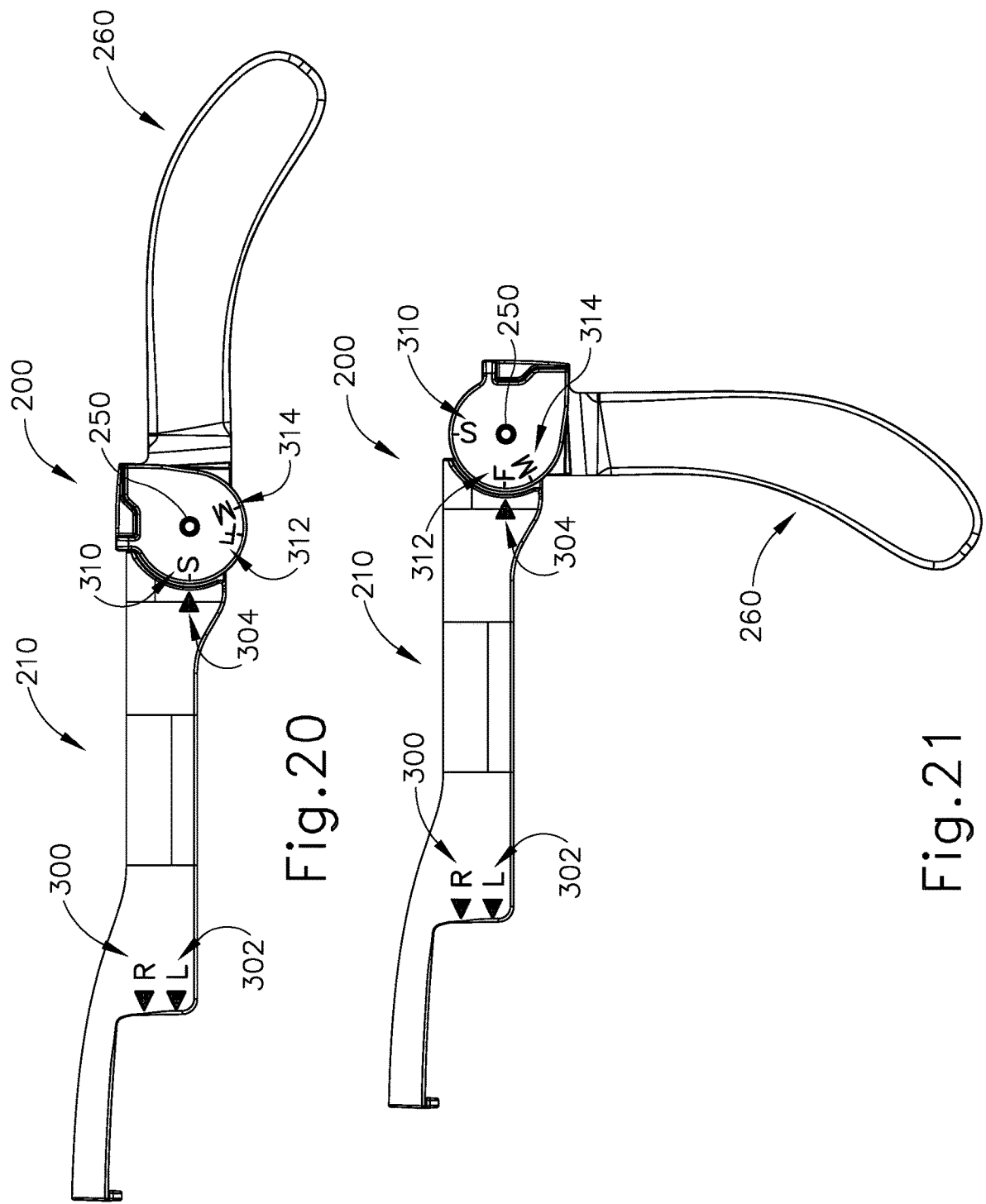

APPARATUS FOR BENDING MALLEABLE GUIDE OF SURGICAL INSTRUMENT

This application is a division of U.S. application Ser. No. 14/928,260, filed Oct. 30, 2015, issued as U.S. Pat. No. 10,137,286 on Nov. 27, 2018, entitled "Apparatus for Bending Malleable Guide of Surgical Instrument."

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, now U.S. Pat. No. 9,155,492, issued Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

It may be desirable to provide transcutaneous illumination that is more easily visible in relation to ambient light. While several systems and methods have been made to illuminate guidewire, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 8 depicts an exploded perspective view of the bending instrument of FIG. 6;

FIG. 9A depicts a perspective view of the bending instrument of FIG. 6 in the non-bending configuration;

FIG. 10A depicts a cross-sectional side view of the bending instrument of FIG. 6, taken along line 10A-10A of FIG. 9A;

FIG. 18 depicts a cross-sectional end view of the bending instrument of FIG. 6 coupled with the dilation instrument of FIG. 1, taken along line 18-18 of FIG. 7A;

FIG. 19 depicts an enlarged cross-sectional end view of the malleable guide member of FIG. 3 received in a trough of the bending instrument of FIG. 6;

FIG. 20 depicts a side elevational view of the bending instrument of FIG. 6, with an actuator member in a first angular relationship with the grounding member of FIG. 12;

FIG. 21 depicts a side elevational view of the bending instrument of FIG. 6, with an actuator member in a second angular relationship with the grounding member of FIG. 12;

Figure 1A:
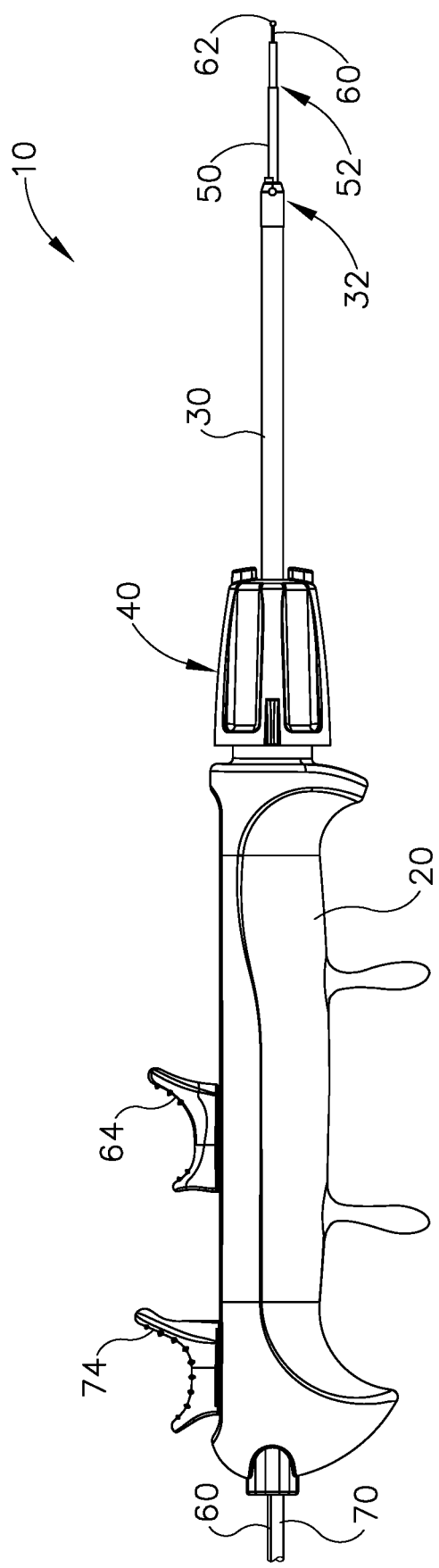
FIG. 1A depicts a side elevational view of an exemplary dilation instrument, in an initial configuration.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. EXEMPLARY DILATION INSTRUMENT

Figure 1B:
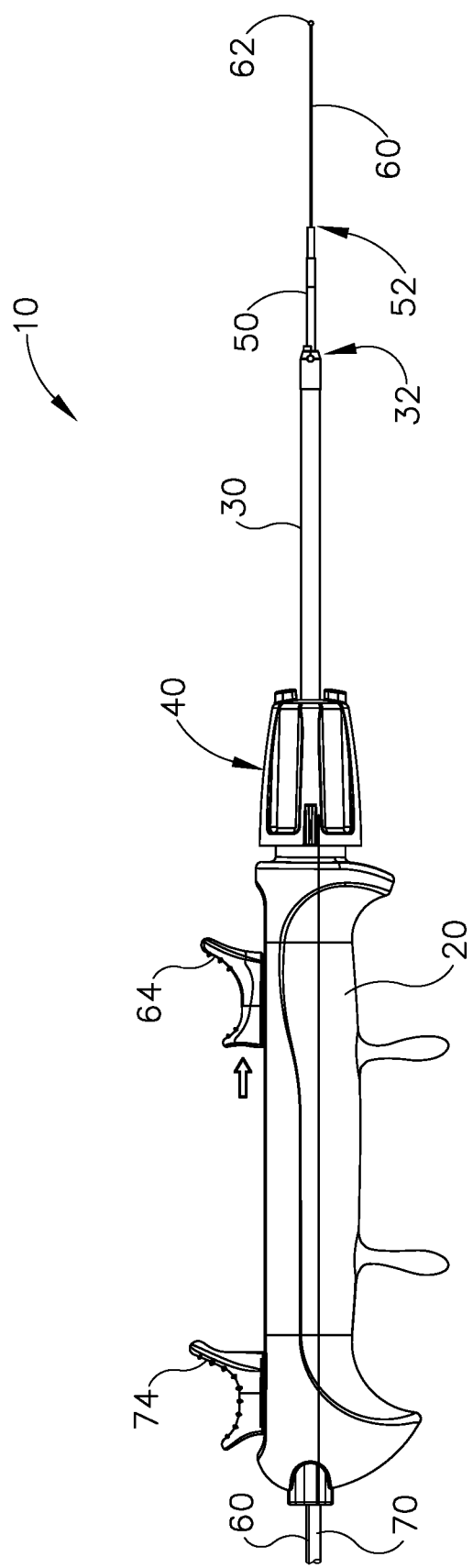
FIG. 1B depicts a side elevational view of the dilation instrument of FIG. 1A, with a guidewire advanced to a distal position.
Figure 1C:
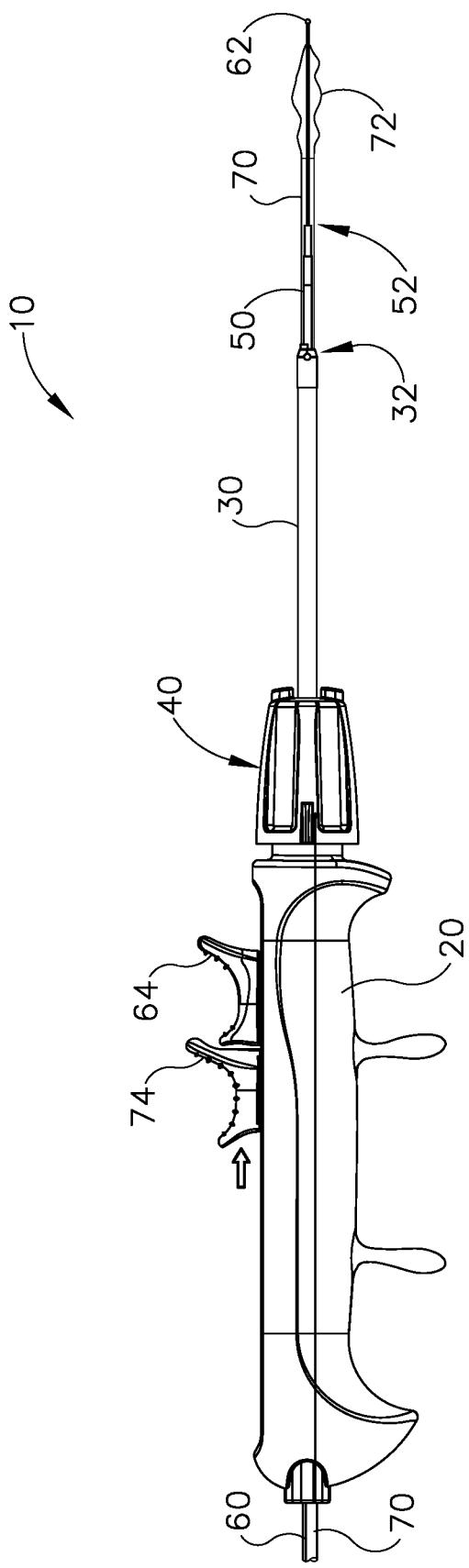
FIG. 1C depicts a side elevational view of the dilation instrument of FIG. 1A, with a dilation catheter advanced to a distal position.

FIGS. 1A-1C show an exemplary dilation instrument (10) that may be used to dilate the ostium of a paranasal sinus; or to dilate some other anatomical passageway (e.g., within the ear, nose, or throat, etc.). By way of example only, dilation instrument (10) may be configured and operable in accordance with at least some of the teachings of U.S. Pub. No. 2012/0071857, entitled "Methods and Apparatus for Treating Disorders of the Sinuses," published Mar. 22, 2012, now abandoned, the disclosure of which is incorporated by reference herein. In addition or in the alternative, dilation instrument (10) may be configured and operable like the Relieva Scout® Sinus Dilation System by Acclarent, Inc. of Menlo Park, Calif.

Dilation catheter system (10) of the present example comprises a handle assembly (20), a rigid guide member (30), a rotary knob (40), a malleable guide member (50), a guidewire (60), and a dilation catheter (70). Handle assembly (20) is configured to be gripped by a single hand of an operator. Rigid guide member (30) extends distally from handle assembly (20) and is substantially straight. In some versions, rigid guide member (30) is formed of metal, though any other suitable material(s) may be used. In the present example, the longitudinal position and angular position of rigid guide member (30) is fixed relative to handle assembly (20).

Malleable guide member (50) protrudes distally from the open distal end (32) of rigid guide member (30). The outer diameter of malleable guide member (50) is smaller than the inner diameter of rigid guide member (30), such that a cylindraceous gap is defined between the outer diameter of malleable guide member (50) and the inner diameter of rigid guide member (30). This cylindraceous gap is sized to accommodate a translating dilation catheter (70) as will be described in greater detail below. While malleable guide member (50) is shown as having a straight configuration in FIGS. 1A-1C, malleable guide member (50) may be bent to various bend angles as shown in FIGS. 2A, and 3-5; and as will be described in greater detail below. Malleable guide member (50) is configured to substantially maintain a bend angle once bent, until the operator takes steps to intentionally unbend or re-bend malleable guide member (50). In other words, malleable guide member (50) has sufficient rigidity to maintain a selected bend angle during operation of dilation instrument (10) in a dilation procedure, such that use of dilation instrument (10) in a dilation procedure will not cause malleable guide member (50) to undesirably unbend or re-bend. In the present example, malleable guide member (50) is formed of metal, though any other suitable material(s) may be used. While the term "malleable" is used to describe guide member (50), that term should not be read as requiring guide member (50) to have undergone an annealing process or any other process to increase the ductility of steel. In some instances, rigid guide member (30) and malleable guide member (50) are formed of the exact same material (e.g., full hard stainless steel), yet the differences in size and thickness provide greater rigidity in guide member (30) than in guide member (50).

Guidewire (60) is slidably received in a central lumen defined in malleable guide member (50). Guidewire (60) includes a rounded tip feature (62) that is located distal to the open distal end (52) of malleable guide member (50). Guidewire (60) is secured to a slider (64), which is slidably coupled with handle assembly (20). Slider (64) is thus operable to slide guidewire (60) between a proximal position (FIG. 1A) and a distal position (FIG. 1B). In the present example, tip feature (62) has an outer diameter that is larger than the inner diameter of distal end (52) of malleable guide member (50), such that tip feature (62) cannot be retracted proximally back through malleable guide member (50). In some versions, guidewire (60) includes one or more optical fibers, and tip feature (62) is configured to emit light communicated through such optical fibers. This may enable an operator to verify positioning of tip feature (62) within a sinus cavity through a transillumination effect as is known in the art. The proximal end of guidewire (60) may be coupled with a suitable light source. By way of example only, guidewire (60) may be configured and operable in accordance with at least some of the teachings of U.S. Pub. No. 2012/0078118, now U.S. Pat. No. 9,155,492, issued Oct. 13, 2015, the disclosure of which is incorporated by reference herein. In addition or in the alternative, guidewire (60) may be configured and operable like the Relieva Luma Sentry® Sinus Illumination System by Acclarent, Inc. of Menlo Park, Calif. Other suitable forms that guidewire (60) may take will be apparent to those of ordinary skill in the art in view of the teachings herein.

Figure 2A:
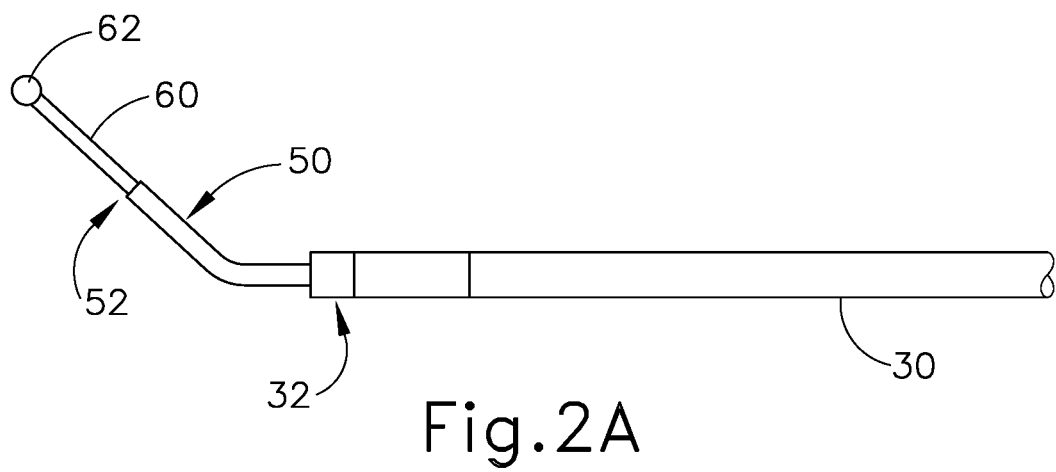
FIG. 2A depicts a side elevational view of the distal end of the dilation instrument of FIG. 1A, with the guidewire advanced to the distal position.
Figure 2B:
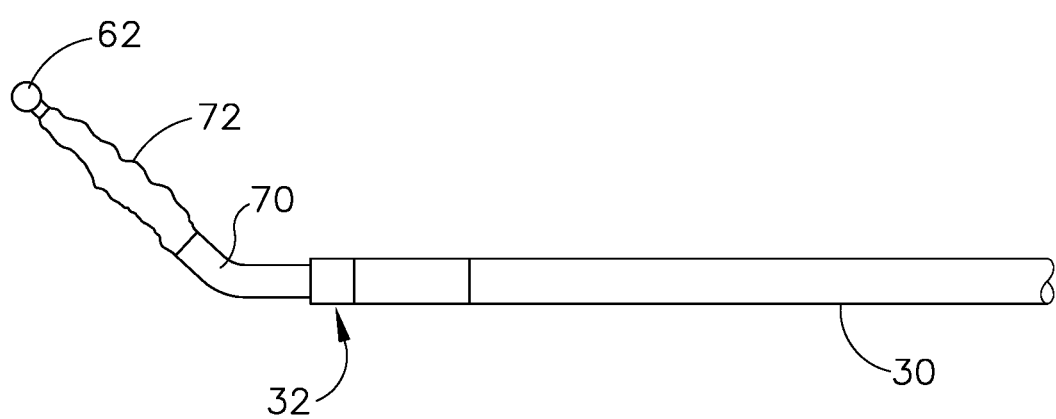
FIG. 2B depicts a side elevational view of the distal end of the dilation instrument of FIG. 1A, with a dilation catheter advanced to a distal position.

Dilation catheter (70) is slidably disposed along malleable guide member (50) and is thus operable to translate through the cylindraceous gap is defined between the outer diameter of malleable guide member (50) and the inner diameter of rigid guide member (30). Dilation catheter (70) is secured to a slider (74), which is slidably coupled with handle assembly (20). Slider (74) is thus operable to slide dilation catheter (70) between a proximal position (FIGS. 1B and 2A) and a distal position (FIGS. 1C and 2B). When dilation catheter (70) translates from the proximal position to the distal position dilation catheter (70) passes over the open distal end (52) of malleable guide member (50) and then traverses along at least a portion of the length of guidewire (60) that extends distally from open distal end (52) of malleable guide member (50). In some versions, dilation instrument (10) is configured such that dilation catheter (70) is unable to translate distally to a position where the distal end of dilation catheter (70) is distal to tip feature (62) of guidewire (60). For instance, slider (74) may engage slider (64) when dilation catheter (70) is driven to a distal-most position, and this engagement between sliders (64, 74) may prevent the distal end of dilation catheter (70) from engaging or otherwise passing distally over tip feature (62) of guidewire (60). This engagement may also enable slider (74) to be used to advance a proximally positioned guidewire (60) and dilation catheter (70) distally simultaneously, since slider (74) would drive a proximally positioned slider (64) distally. Thus, instrument (10) need not necessarily be operated in a manner where guidewire (60) is advanced distally, as a discrete act in a sequence, before dilation catheter (70) is advanced distally.

Figure 2C:
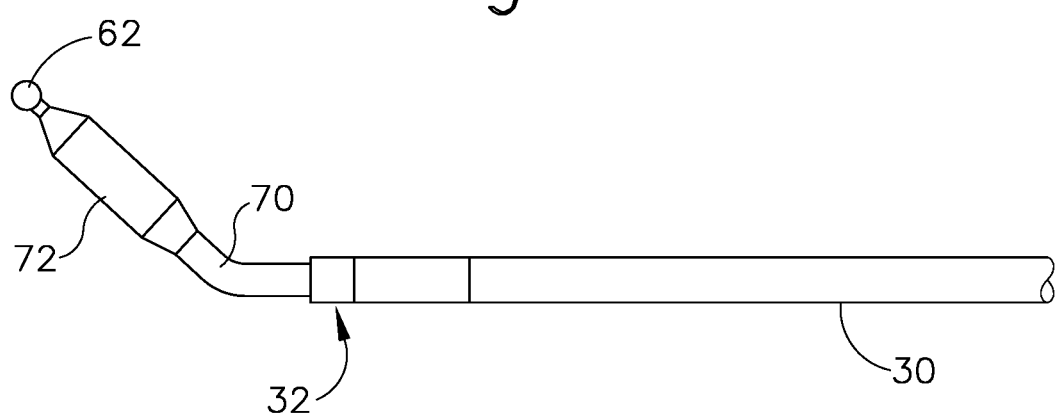
FIG. 2C depicts a side elevational view of the distal end of the dilation instrument of FIG. 1A, with a dilator of the dilation catheter in an expanded state.

The distal end of dilation catheter (70) comprises a dilator (72). Dilator (72) is operable to transition between a non-expanded state (FIG. 2B) and an expanded state (FIG. 2C). In the non-expanded state, dilator (72) may be inserted into a sinus ostium or other drainage passageway associated with a paranasal sinus. Dilator (72) may then be expanded to dilate the sinus ostium or other drainage passageway as described in various references herein. In the present example, dilator (72) comprises an inflatable balloon that receives saline (or some other fluid) for inflation, though it should be understood that dilator (72) may instead take a variety of other forms. In some versions, dilation catheter (70) is fluidly coupled with an inflator instrument that is constructed and operable in accordance with at least some of the teachings of U.S. Pub. No. 2014/0074141, entitled "Inflator for Dilation of Anatomical Passageway," published Mar. 13, 2014, now U.S. Pat. No. 9,962,530, issued Aug. 8, 2015, the disclosure of which is incorporated by reference herein.

Figure 3:
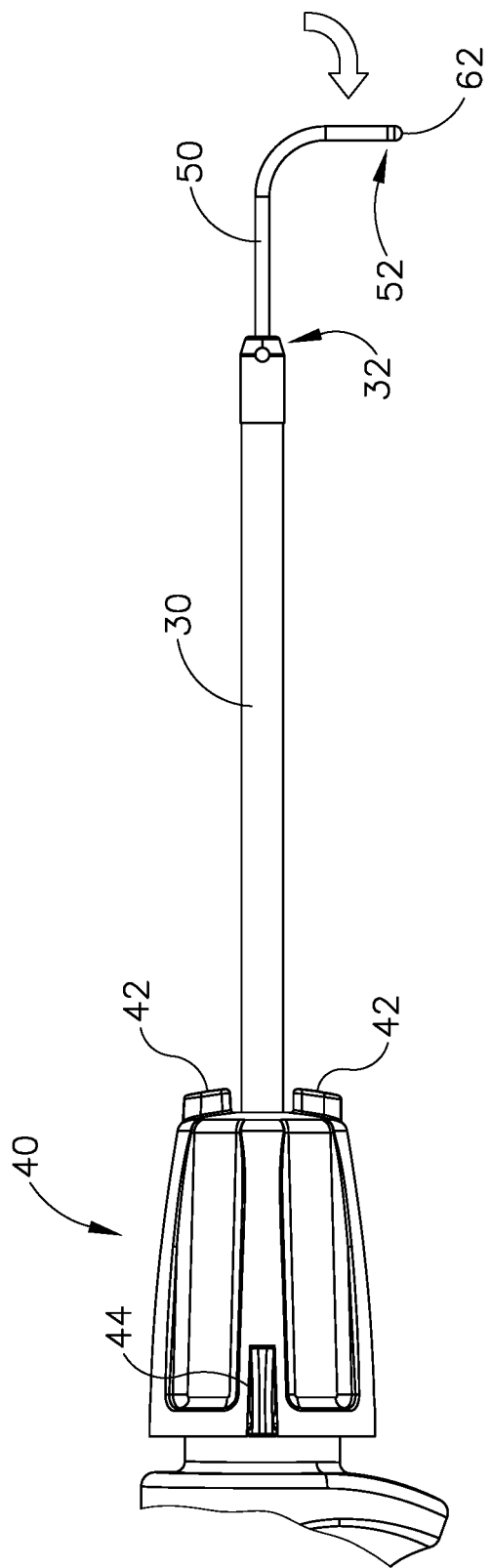
FIG. 3 depicts a side elevational view of a shaft assembly of the dilation instrument of FIG. 1A, with a malleable guide member bent downwardly.
Figure 4:
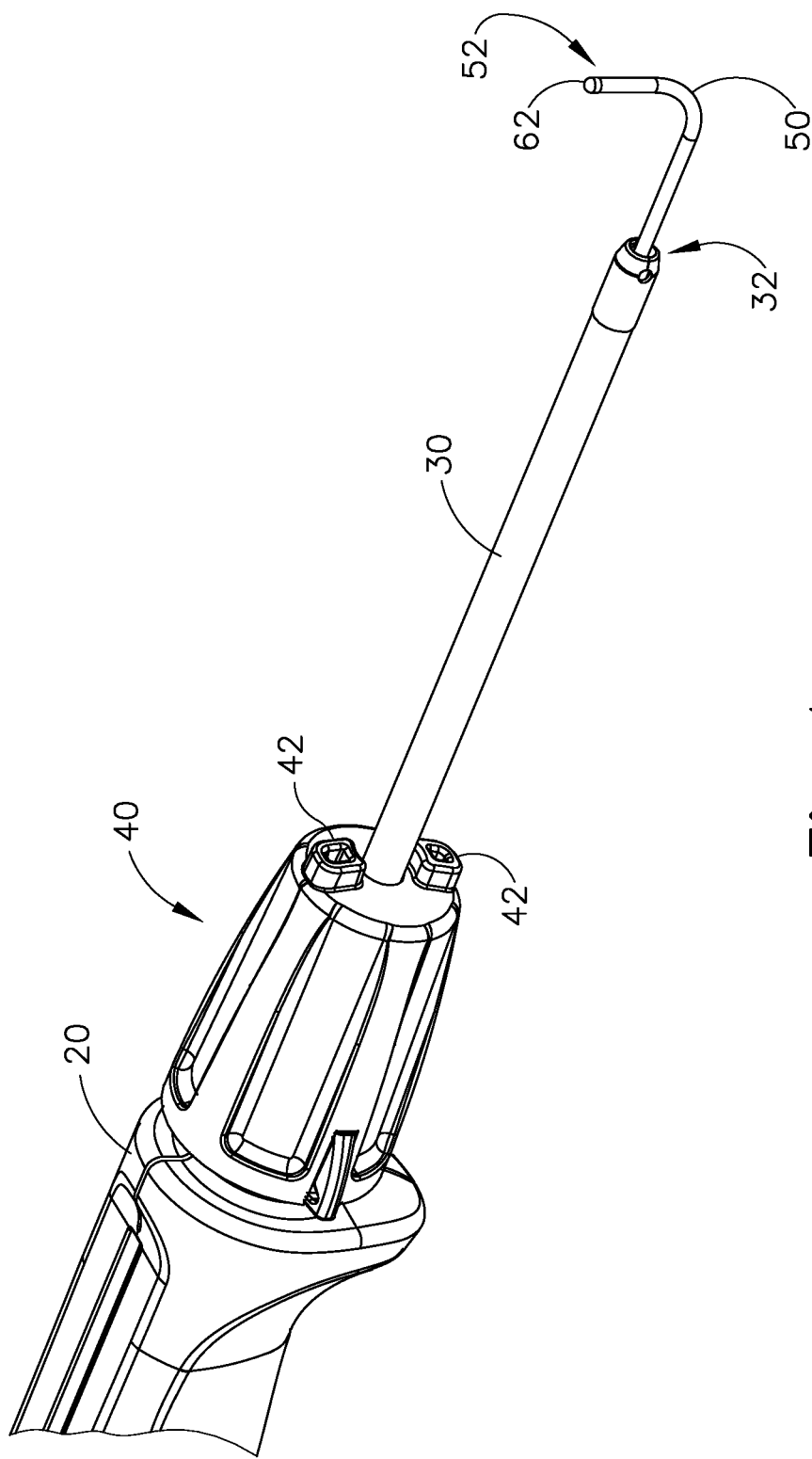
FIG. 4 depicts a perspective view of the shaft assembly of FIG. 3, with the malleable guide member bent upwardly.
Figure 5:
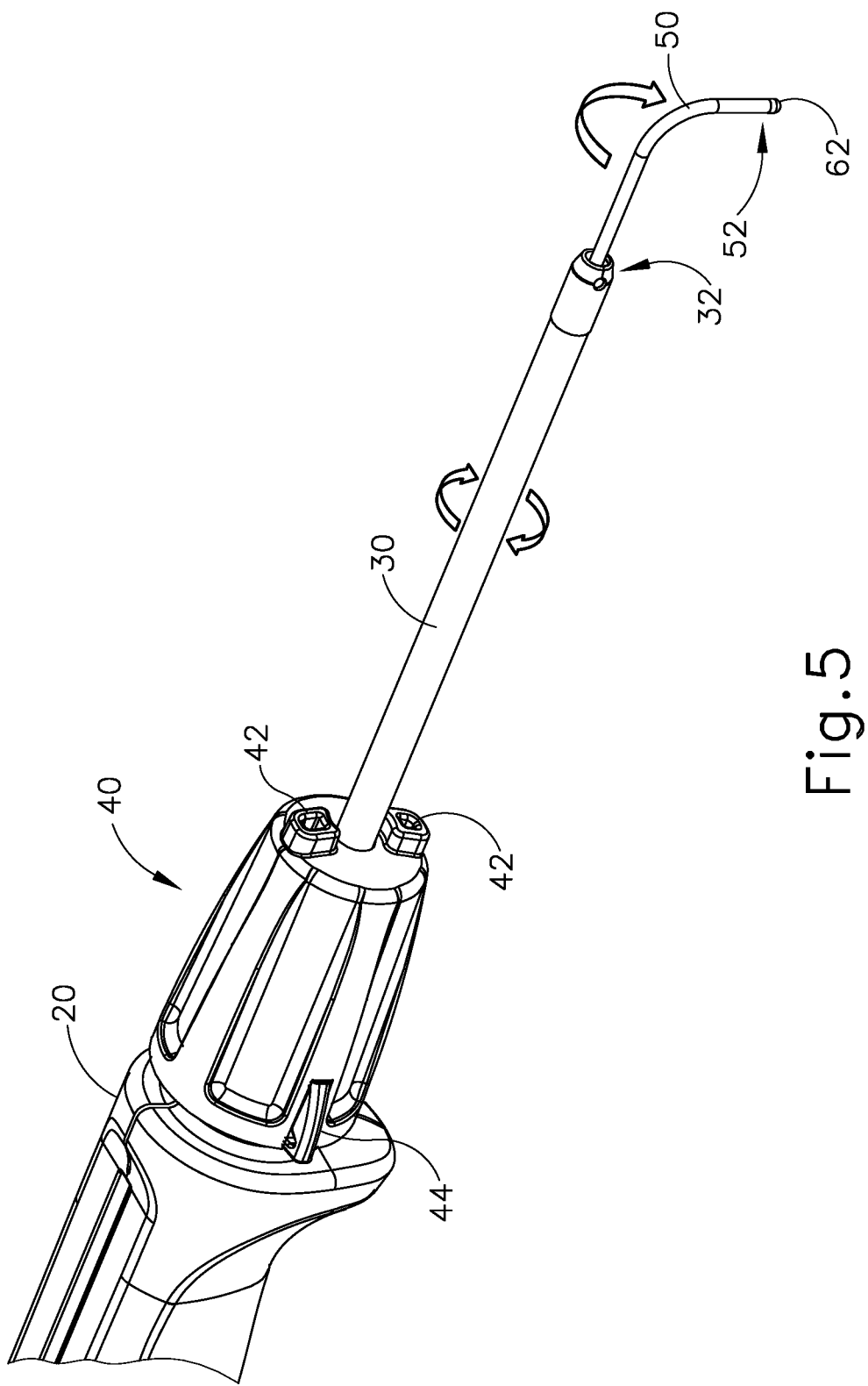
FIG. 5 depicts a perspective view of the shaft assembly of FIG. 3, with the shaft assembly rotated to re-orient the malleable guide member downwardly.
Figure 6:
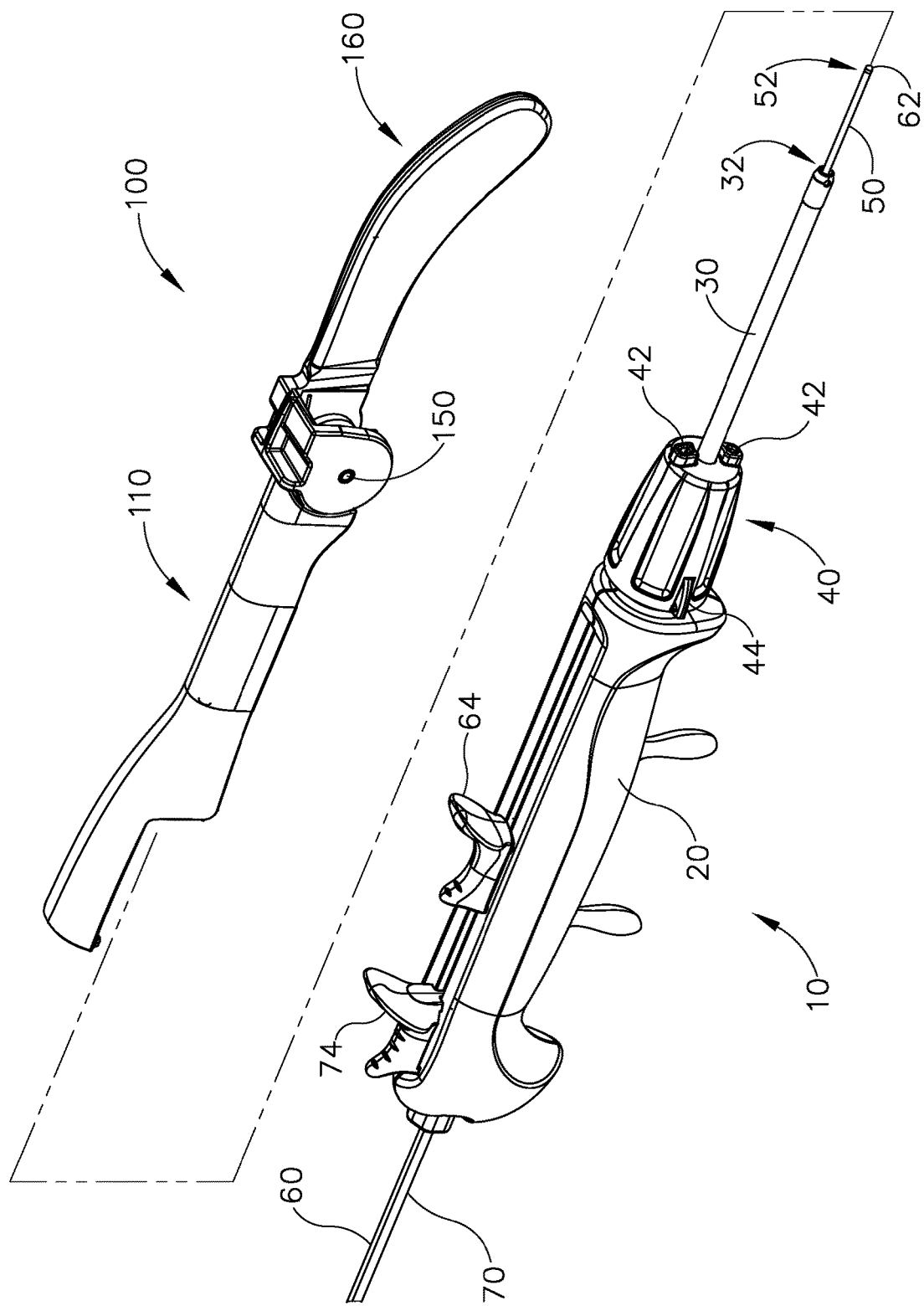
FIG. 6 depicts a perspective view of the dilation instrument of FIG. 1A, with a bending instrument separated therefrom.
Figure 7A:
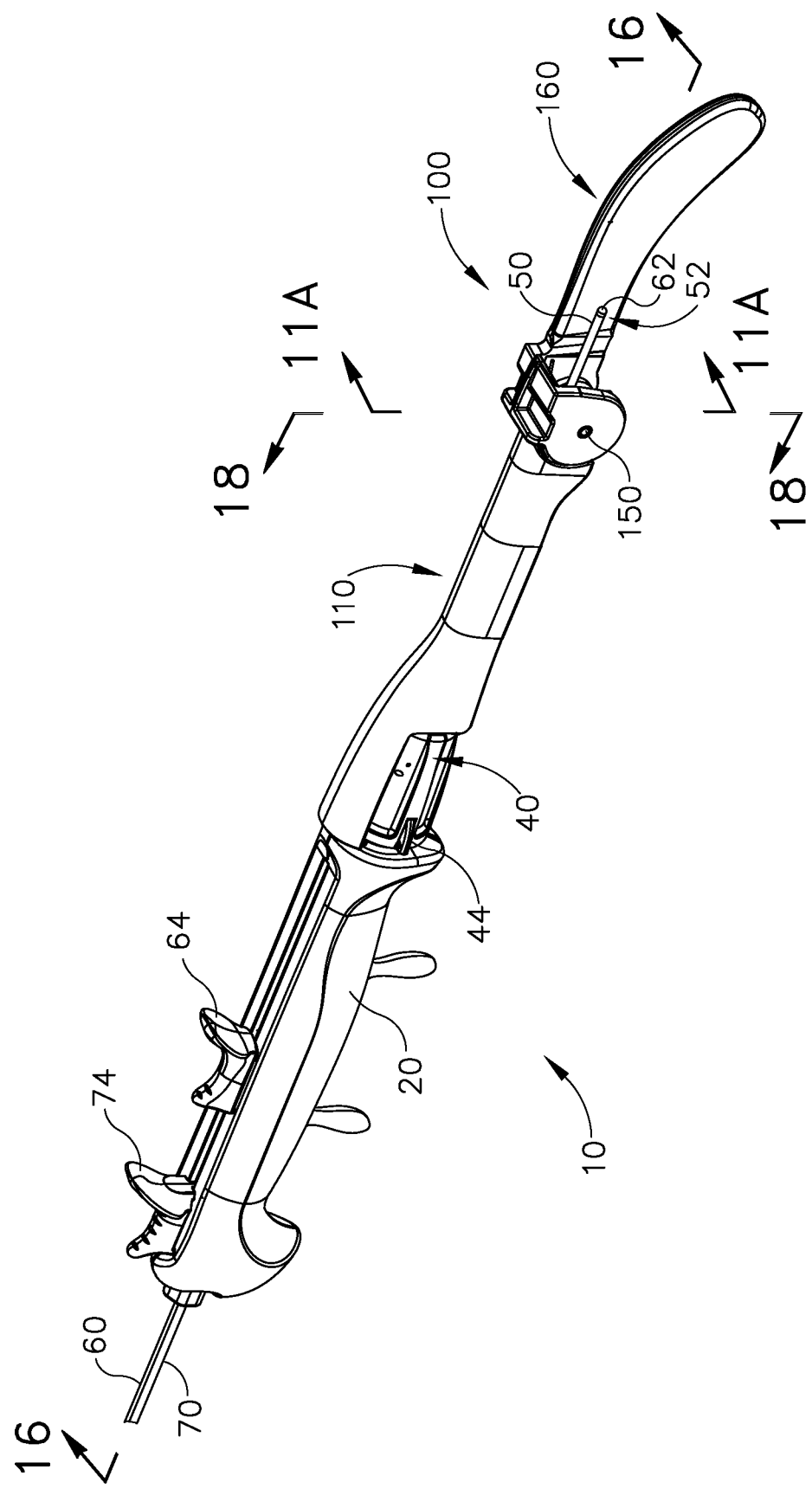
FIG. 7A depicts a perspective view of the bending instrument of FIG. 6 coupled with the dilation instrument of FIG. 1A, with the bending instrument in a non-bending configuration.
Figure 7B:
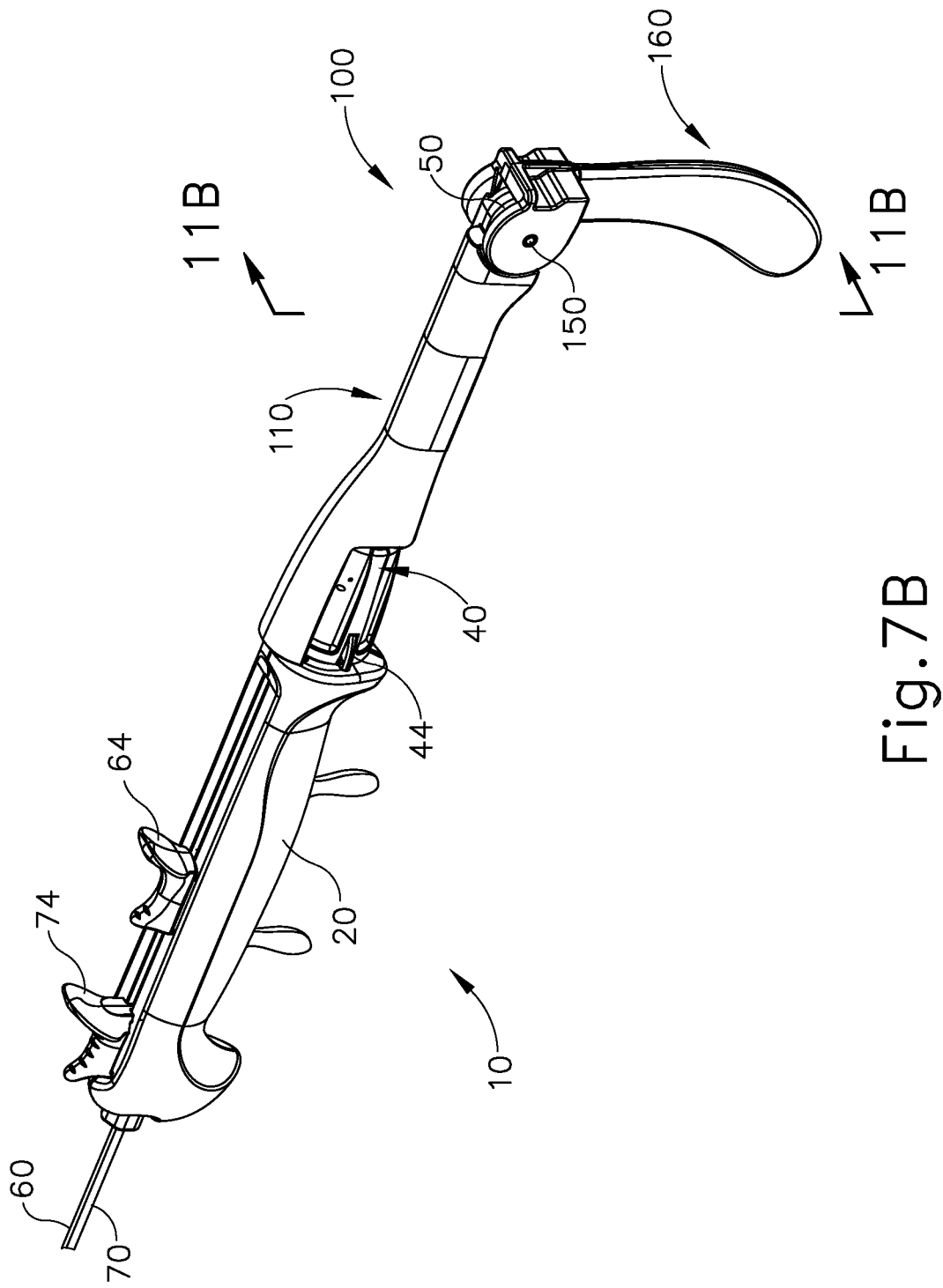
FIG. 7B depicts a perspective view of the bending instrument of FIG. 6 coupled with the dilation instrument of FIG. 1A, with the bending instrument in a bending configuration.

Rotary knob (40) is fixedly secured to the proximal end of malleable guide member (50). As shown in FIGS. 3 and 5, rotary knob (40) includes a pair of distally projecting bosses (42) and a laterally projecting indicator fin (44). Bosses (42) are angularly spaced from each other by 180° about the longitudinal axis of rigid guide member (30). Rotary knob (40) is configured to rotate and translate about rigid guide member (30), though the degree of rotation and the degree of translation are limited. In particular, as shown in FIGS. 4-5, rotary knob (40) is configured to rotate through an angular range of 180° about the longitudinal axis of rigid guide member (30). In the present example, this angular range provides rotation of rotary knob (40) between a position where indicator fin (44) is located at the 3 o'clock angular position (i.e., pointing to the right when viewing instrument (10) from the distal end toward the proximal end, as shown in FIG. 4) and a position where indicator fin (44)

is located at the 9 o'clock angular position (i.e., pointing to the right when viewing instrument (10) from the distal end toward the proximal end, as shown in FIGS. 1A-1C, 3, 5-7B, and 17-18). In the present example, an operator would rotate rotary knob (40) based on whether the operator is grasping instrument (10) with their left hand or right hand, as will be described in greater detail below.

As also shown in FIGS. 4-5, rotation of rotary knob (40) also rotates malleable guide member (50), thereby re-orienting distal end (52) of malleable guide member (50) and tip feature (62) of guidewire (60). An operator may wish to provide such rotation and re-orientation based on the sinus in which guidewire (60) and dilation catheter (70) are to be inserted. In addition or in the alternative, an operator may wish to provide such rotation and re-orientation in order to facilitate right-handed use or left-handed use of dilation instrument (10).

In the present example, the angular position of rotary knob (40) and malleable guide member (50) is selectively locked or unlocked based on longitudinal positioning of rotary knob (40) relative to handle assembly (20). In particular, when rotary knob (40) is in a distal longitudinal position, the angular position of rotary knob (40) and malleable guide member (50) is locked. When rotary knob (40) is in a proximal longitudinal position, the angular position of rotary knob (40) and malleable guide member (50) is unlocked. A resilient member biases rotary knob (40) to the distal position. Thus, in order to rotate rotary knob (40) and malleable guide member (50) about the longitudinal axis of rigid guide member (30), the operator may grasp rotary knob (40), pull rotary knob (40) proximally, rotate rotary knob (40) to achieve a desired angular position while still pulling rotary knob (40) proximally, then release rotary knob (40) to allow rotary knob (40) to return to the distal position. Various suitable structural features that may be incorporated into instrument to provide this functionality will be apparent to those of ordinary skill in the art in view of the teachings herein. Also, in the present example, rotary knob (40) provides three discrete angular locking positions (e.g., 12 o'clock, 3 o'clock, and 9 o'clock). However, some other versions may provide additional discrete angular locking positions.

In some instances, dilation instrument (10) is used in combination with an endoscope, which provides visualization in the sinus cavity of the patient. The operator may thus position dilation instrument (10) at the appropriate sinus ostium, other outflow tract, etc., under visual guidance from the endoscope. By way of example only, such an endoscope may be configured and operable in accordance with at least some of the teachings of U.S. Pub. No. 2010/0030031, now abandoned, the disclosure of which is incorporated by reference herein. In addition or in the alternative, such an endoscope may be configured and operable like the Acclarent Cyclops™ Multi-Angle Endoscope by Acclarent, Inc. of Menlo Park, Calif. Of course, any other suitable kind of device(s) may be used to provide visualization during use of dilation instrument (10).

II. EXEMPLARY BENDING INSTRUMENT

FIGS. 6-19 show an exemplary bending instrument (100) that may be coupled with dilation instrument (10) to bend malleable guide member (50) to consistently achieve a selected bend angle. While bending instrument (100) is described herein as being used with dilation instrument (10), it should be understood that bending instrument (100) may be used with other kinds of instruments that have a malleable guide feature where an operator may wish to provide precision, certainty, and consistency in achieving a desired bend angle in the malleable guide feature. By way of example only, bending instrument (100) may be used with the dilation instrument disclosed in U.S. patent application Ser. No. 14/824,435, entitled "Balloon Dilation System with Malleable Internal Guide," filed Aug. 12, 2015, now U.S. Pat. No. 10,137,286, issued Nov. 27, 2018, the disclosure of which is incorporated by reference herein.

Figure 9B:
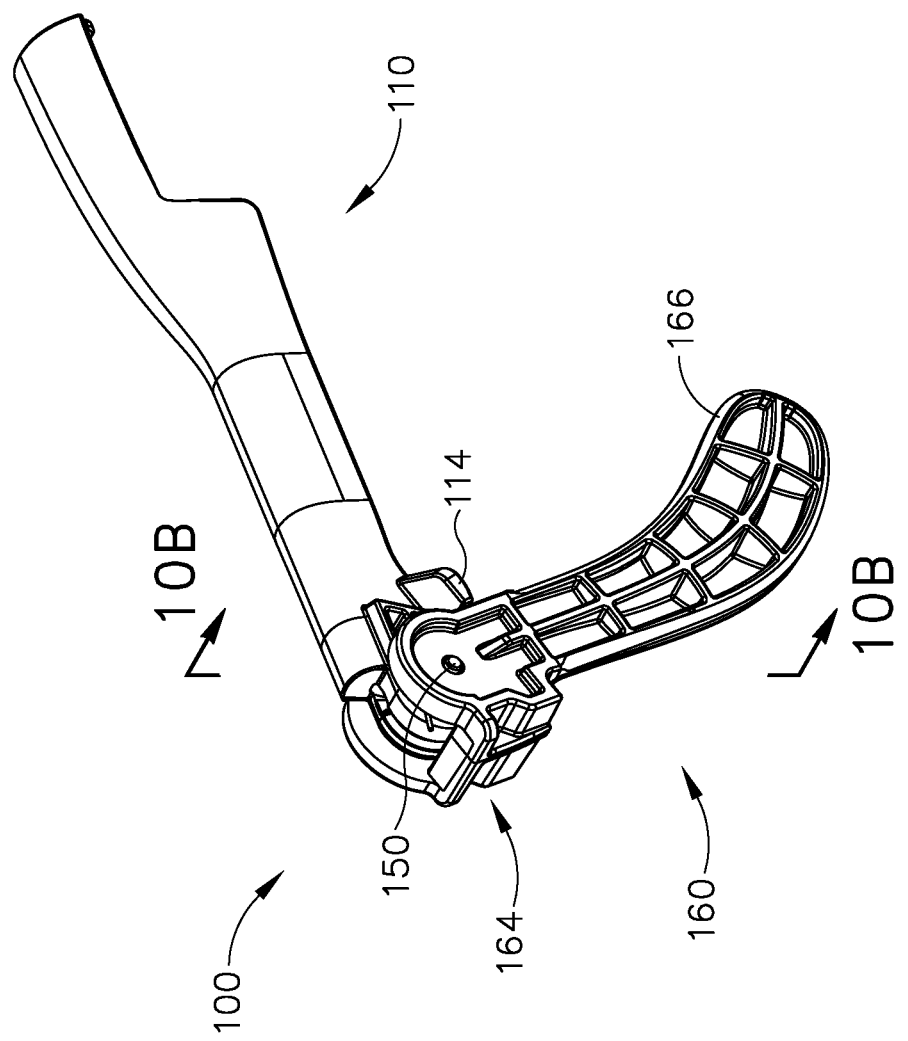
FIG. 9B depicts a perspective view of the bending instrument of FIG. 6 in the bending configuration.
Figure 10B:
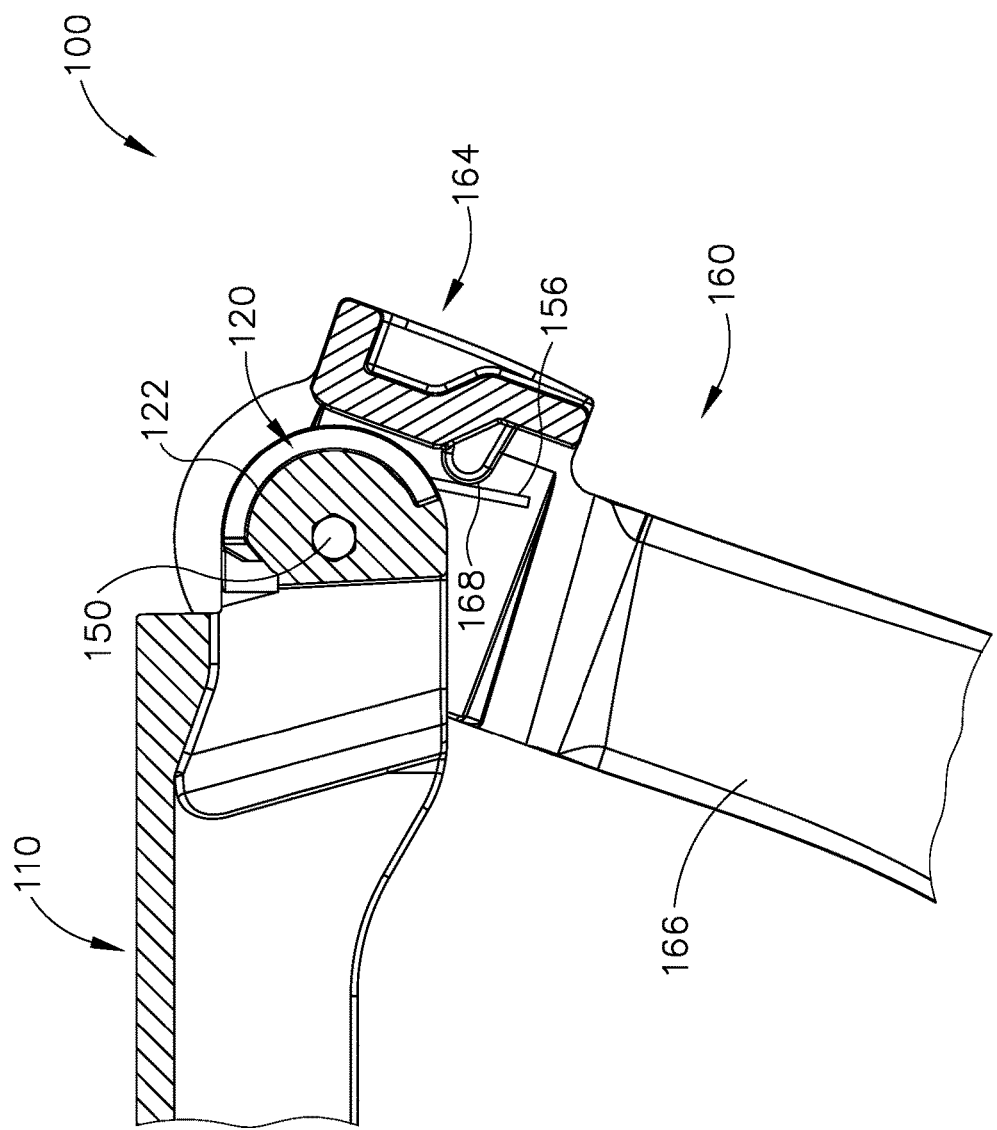
FIG. 10B depicts a cross-sectional side view of the bending instrument of FIG. 6, taken along line 10B-10B of FIG. 9B.
Figure 13:
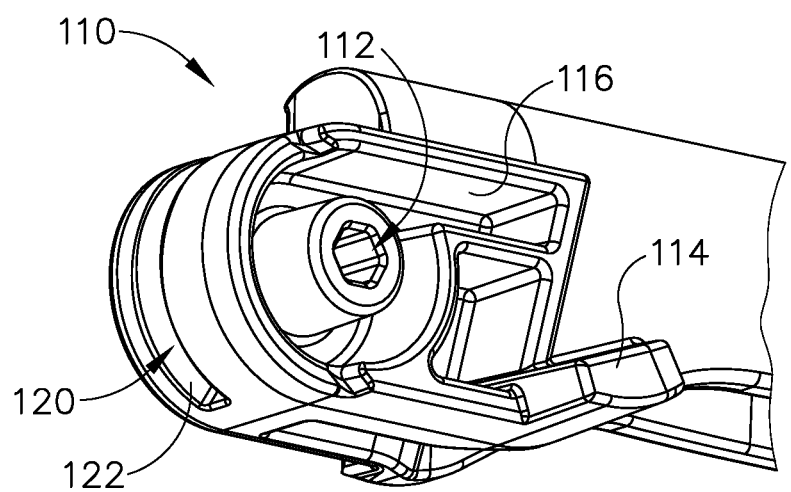
FIG. 13 depicts another perspective view of the distal end of the grounding member of FIG. 12.
Figure 14:
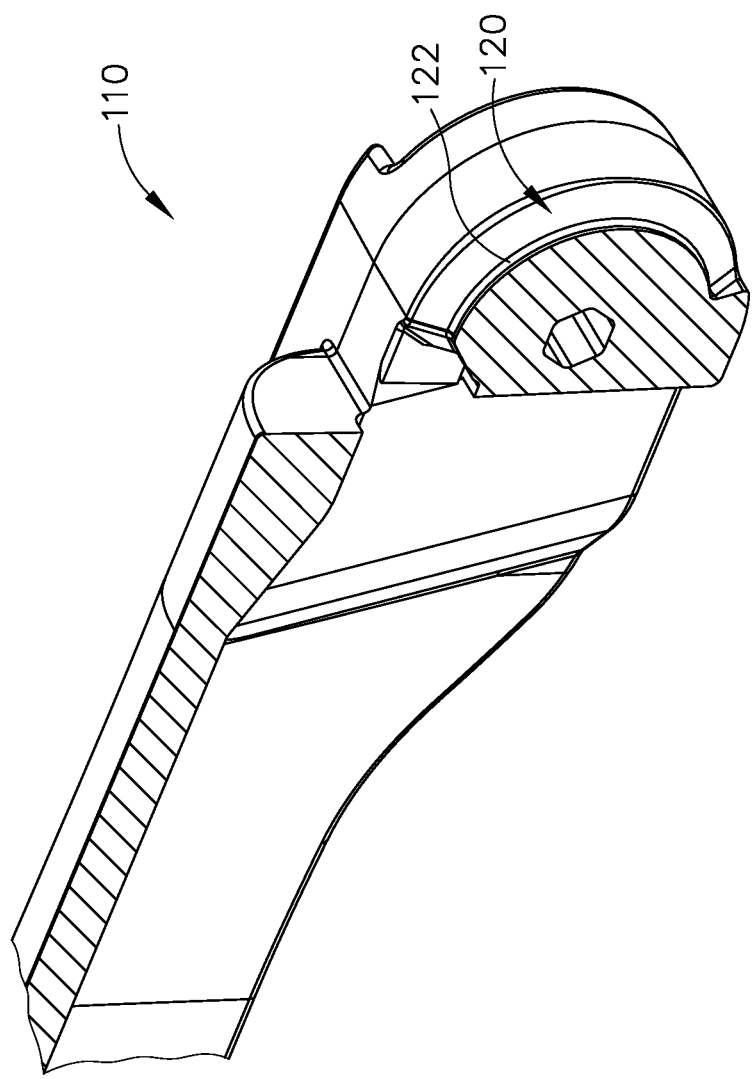
FIG. 14 depicts a cross-sectional perspective view of the distal end of the grounding member of FIG. 12, taken along line 14-14 of FIG. 12.
Figure 15:
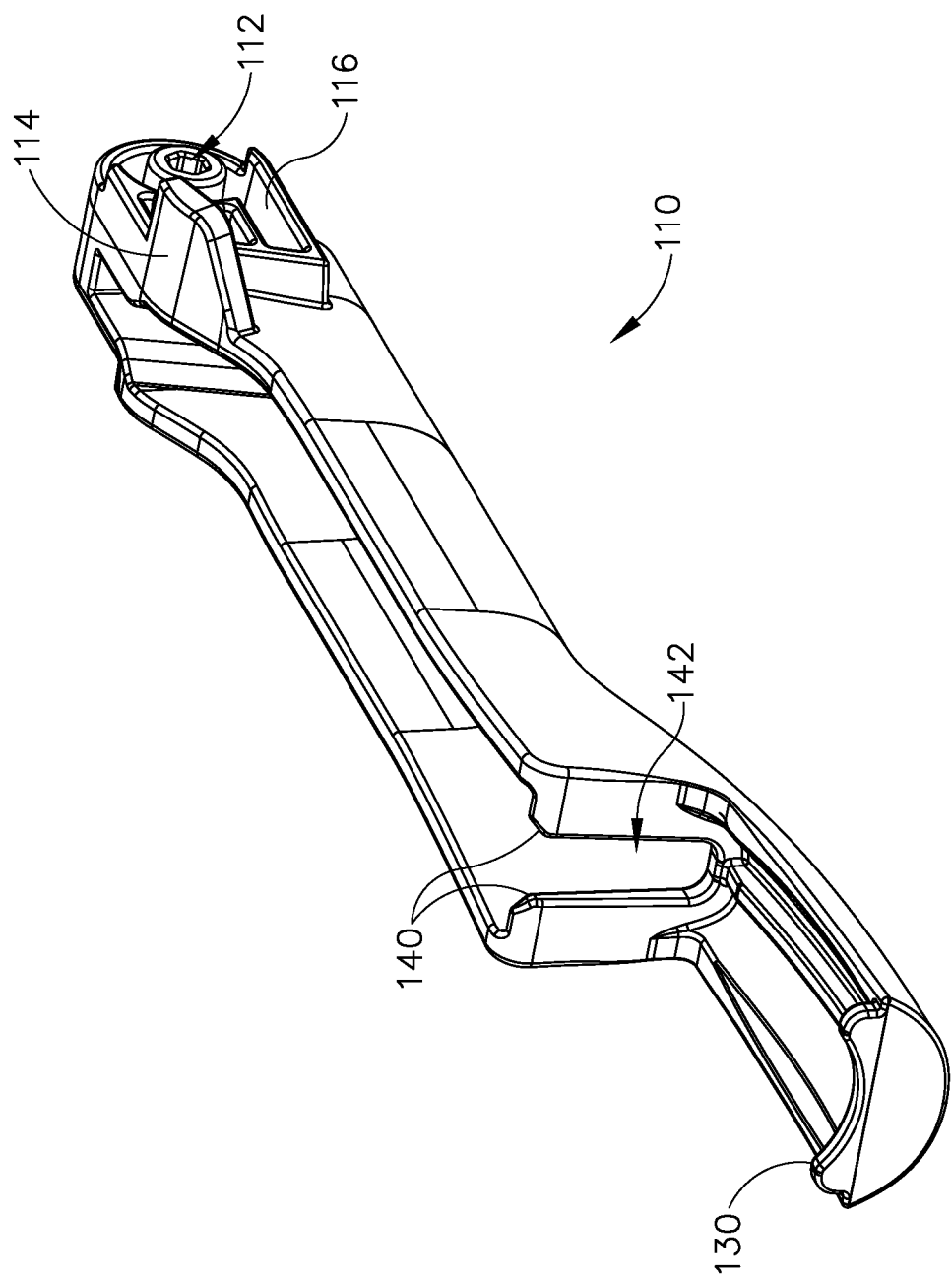
FIG. 15 depicts another perspective view of the grounding member of FIG. 12.

Bending instrument (100) of the present example comprises a grounding member (110) and an actuator (160). As best seen in FIG. 8, grounding member (110) and actuator (160) are pivotably coupled together by a pin (150). Pin (150) is disposed in a pair of openings (162) formed in actuator (160) (FIG. 8); and in an opening (112) formed in grounding member (110) (FIGS. 8, 13, and 15). A torsion spring (152) is coaxially disposed about pin (150) and is configured to resiliently bias actuator (160) to the position shown in FIGS. 6, 7A, 9A, 10A, and 11A; though torsion spring (152) allows an operator to pivot actuator (160) to the position shown in FIGS. 7B, 9B, 10B, and 11B. Torsion spring (152) has one free end (154) that bears against a grounding surface (116) of grounding member (110) (FIG. 13); and another fee end (156) that bears against a grounding feature (168) of actuator (160) (FIGS. 10A-10B). While torsion spring (152) is used to provide a resilient bias to actuator (160) in this example, it should be understood that various other kinds of features (e.g., leaf spring, etc.) may be used to provide a resilient bias to actuator (160).

Actuator (160) of the present example includes a hub (164) where openings (162) are formed; and a paddle (166) that is configured to enable the operator to grasp and pivot actuator (160) relative to grounding member (110). As best seen in FIGS. 9A-9B, grounding member (110) includes a lateral projection (114) that is configured to engage actuator (160) at the junction of hub (164) and paddle (166) when actuator (160) reaches a predefined pivot angle with grounding member (110). Lateral projection (114) thus arrests pivotal movement of actuator (160) relative to grounding member (110). Various suitable pivot angles that may be associated with the positioning and configuration of lateral projection (114) will be apparent to those of ordinary skill in the art. In some instances, the operator wishes to pivot actuator (160) through the full range of motion until lateral projection (114) arrests the motion, to achieve a desired bend angle in malleable guide member (50). Lateral projection (114) thus provides tactile feedback to the operator, indicating that the desired bend angle has been achieved. In some other instances, however, the operator may wish to stop the pivotal movement of actuator (160) short of the position associated with lateral projection (114). In such instances, the operator may rely on visual feedback to determine whether the desired bend angle has been achieved, as described in greater detail below. It should also be understood that additional lateral projections (114) may be used to provide different hard stop locations. In some such versions, lateral projections (114) may be removable from grounding member (110), such that the operator may select and secure the appropriate lateral projection (114) to grounding member based on the anatomical passageway that the operator wishes to access with instrument (10).

Figure 11A:
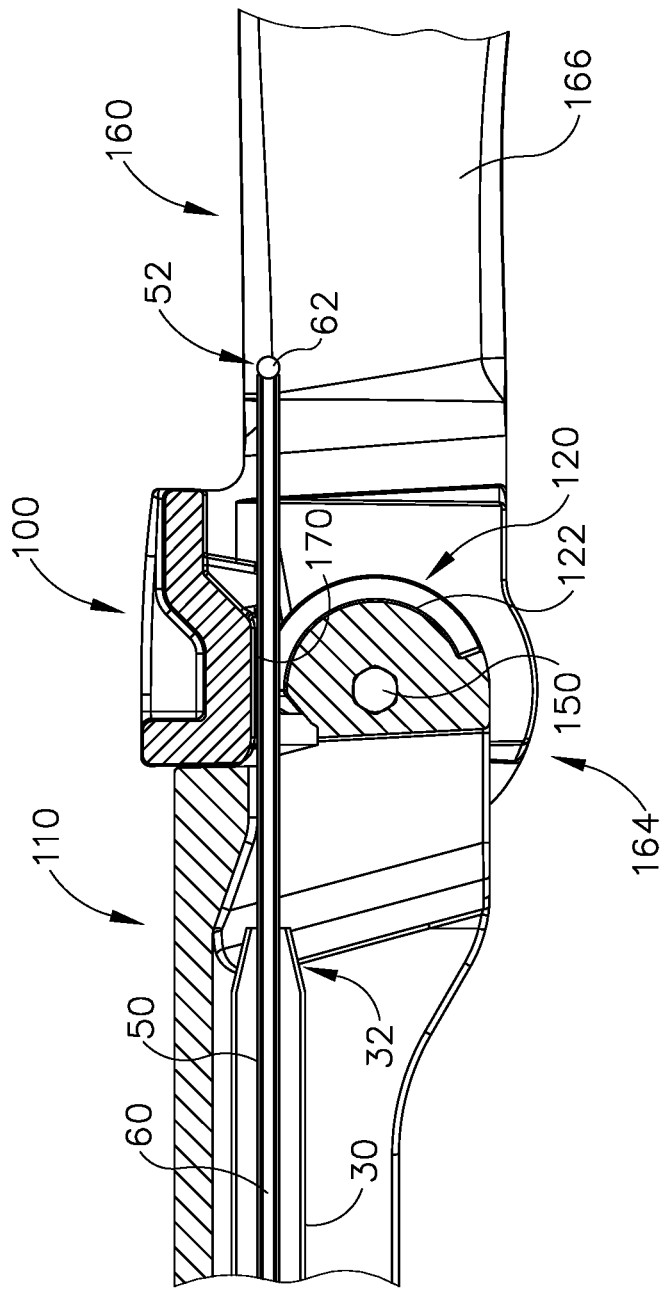
FIG. 11A depicts a cross-sectional side view of the bending instrument of FIG. 6, taken along line 11A-11A of FIG. 7A.
Figure 11B:
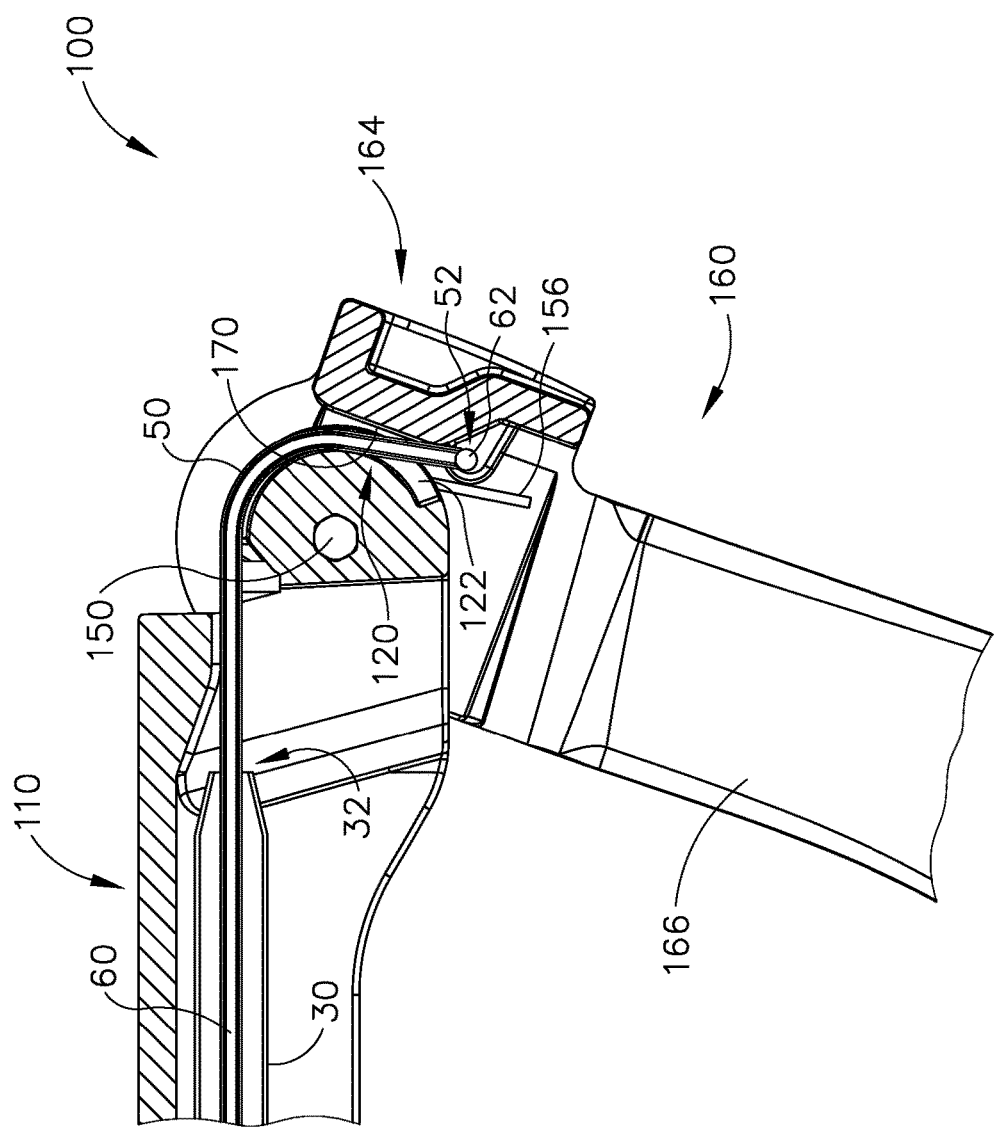
FIG. 11B depicts a cross-sectional side view of the bending instrument of FIG. 6, taken along line 11B-11B of FIG. 7B.
Figure 12:
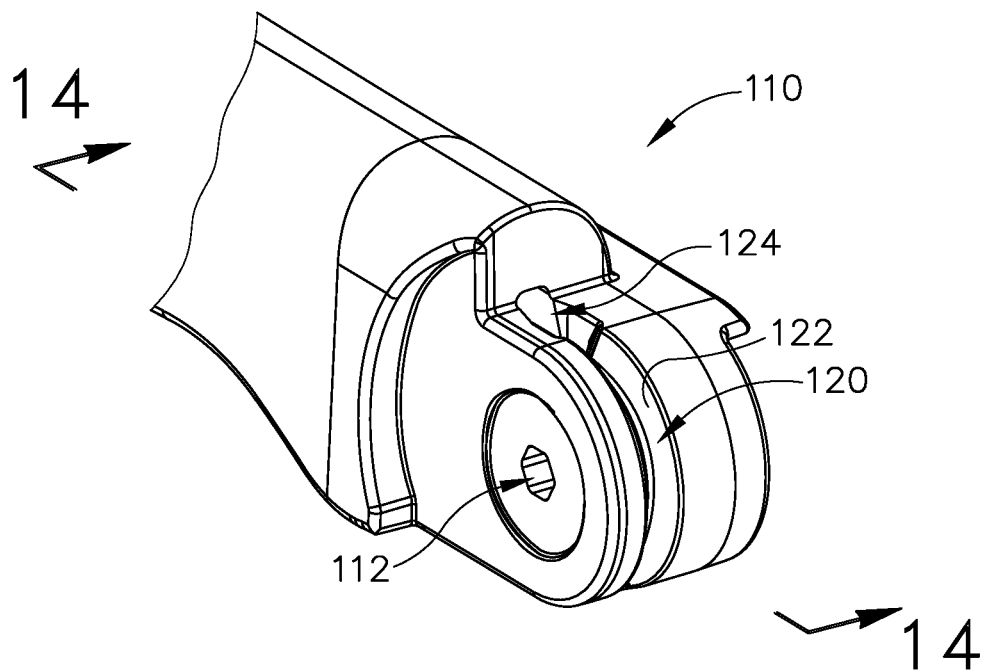
FIG. 12 depicts a perspective view of the distal end of a grounding member of the bending instrument of FIG. 6.

FIGS. 10A-10B show features of bending instrument (100) that engage malleable guide member (50) to thereby bend malleable guide member (50). FIGS. 11A-11B shows those same features engaged with malleable guide member (50). As shown, grounding member (110) comprises a channel (120) that is configured to partially receive malleable guide member (50). As shown in FIG. 12, an opening (124) is located at the proximal end of channel (120). Opening (1240 is sized to allow malleable guide member (50) to pass freely therethrough as bending instrument (100) is being mounted to dilation instrument (10). Actuator (160) comprises a bearing surface (170) that is configured to bear against malleable guide member (50) as actuator (160) is pivoted to the desired angular position. In the present example, bearing surface (170) does not contact malleable guide member (50) when bending instrument (100) is in the non-bending configuration shown in FIGS. 10A and 11A. However, shortly after the operator begins to pivot actuator (160) relative to grounding member (110), bearing surface (170) eventually comes into contact with malleable guide member (50). As the operator continues to pivot actuator (160) relative to grounding member (110), bearing surface (170) bears against malleable guide member (50) and thereby bends malleable guide member along the curve defined by channel (120). It should be understood that bearing surface (170) also slides along a portion of the length of malleable guide member (50) during this bending movement.

In the present example, forming channel (120) is oriented along a plane that is perpendicular to the longitudinal axis of pin (150). Thus, the bent region of malleable guide member (50) extends along a single, flat plane. In some other versions, channel (120) is oriented along a plane that is oblique to the longitudinal axis of pin (150), such that channel (120) traverses a helical path about the longitudinal axis of pin (150). Other suitable forms that channel (120) may take will be apparent to those of ordinary skill in the art in view of the teachings herein.

In order to provide precision, certainty, and consistency in achieving a desired bend angle in malleable guide feature (50), it may be desirable to provide features on bending instrument (100) that mate with features on dilation instrument (10) to substantially secure the position of bending instrument (100) relative to dilation instrument (10) as actuator (160) is pivoted to bend malleable guide feature (50). It may also be desirable for such features to enable bending instrument (100) to be readily coupled with and removed from dilation instrument (10) without interfering with the bend angle achieved in malleable guide feature (50). To these ends, bending instrument (100) of the present example includes a longitudinal grounding feature (130) and a pair of rotational grounding features (140), as shown in FIG. 15. Longitudinal grounding feature (130) is in the form of a saddle-shaped ridge projecting downwardly from the proximal end of grounding member (110). Rotational grounding features (140) comprise a pair of laterally projecting flanges that define a channel (142). In some versions, rotational grounding features (140) are angled such that channel (142) is tapered.

Figure 16:
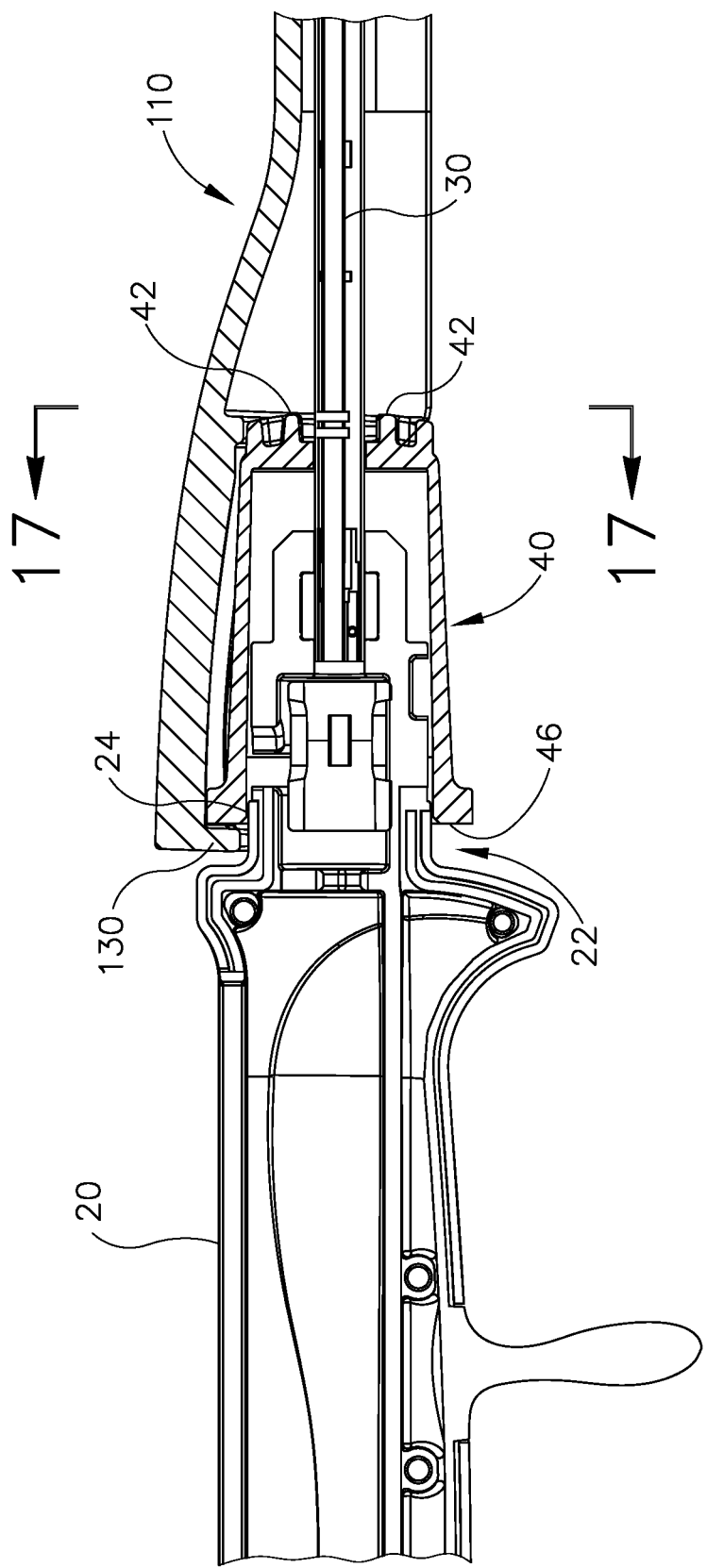
FIG. 16 depicts a cross-sectional side view of the bending instrument of FIG. 6 coupled with the dilation instrument of FIG. 1, taken along line 16-16 of FIG. 7A.

As shown in FIG. 16, longitudinal grounding feature (130) is configured to fit within an annular gap (22) defined between a proximal face (46) of rotary knob (40) and the distal portion of handle assembly (20). The saddle shape of longitudinal grounding feature (130) provides longitudinal grounding feature (130) with a curvature that accommodates the curvature of a distally projecting feature (24) of handle assembly (20), such that longitudinal grounding feature (130) partially wraps around distally projecting feature (24). With distally projecting feature (24) fully seated in annular gap (22), longitudinal grounding feature (130) is configured to abut proximal face (46) of rotary knob (40). This engagement between longitudinal grounding feature (130) and proximal face (46) of rotary knob (40) will prevent bending instrument (100) from moving distally relative to dilation instrument (10) as actuator (160) is pivoted to bend malleable guide member (50). It should also be understood that engagement between longitudinal grounding feature (130) and proximal face (46) of rotary knob (40) will ensure that bending instrument (100) is consistently mounted to dilation instrument (10) at the same longitudinal position each time bending instrument (100) is mounted to dilation instrument (10). Longitudinal grounding feature (130) thus provides consistent longitudinal alignment in addition to providing consistent longitudinal grounding.

Figure 17:
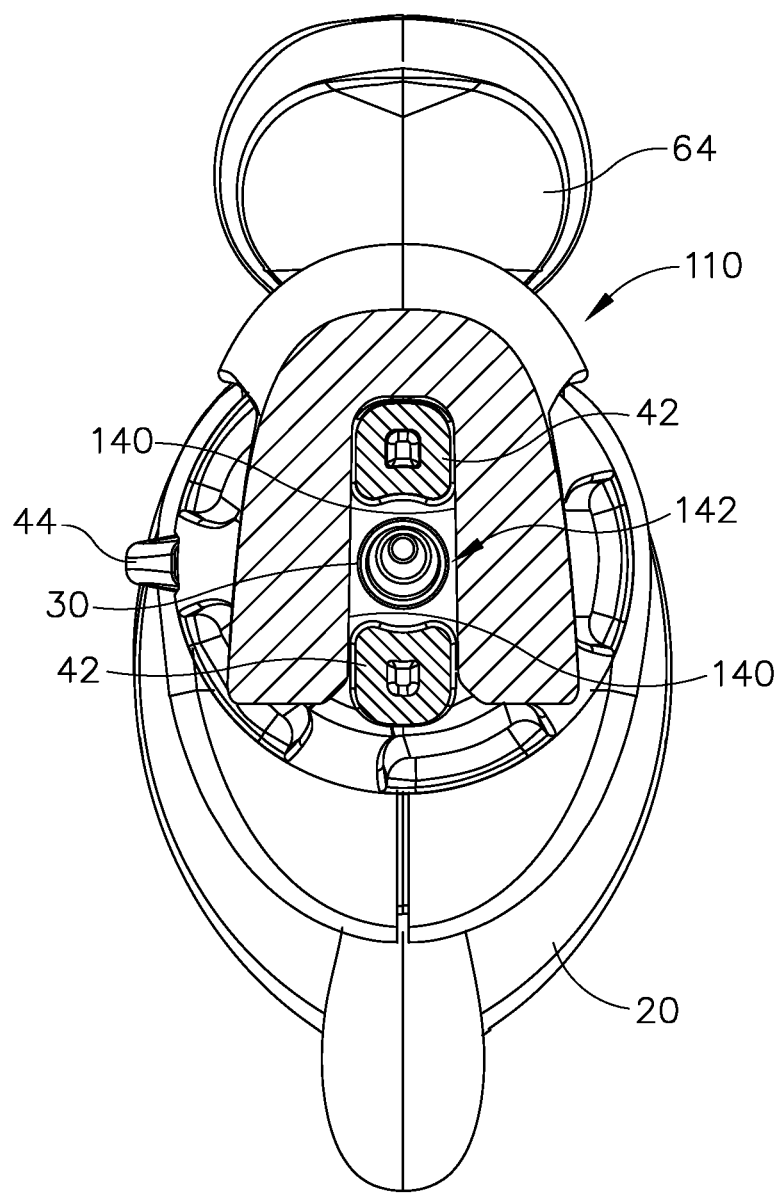
FIG. 17 depicts a cross-sectional end view of the bending instrument of FIG. 6 coupled with the dilation instrument of FIG. 1, taken along line 17-17 of FIG. 16.

As shown in FIG. 17, rotational grounding features (140) are configured to engage the sides of bosses (42) of rotary knob (40). Channel (142) is sized to slidably receive bosses (42). Channel (142) has a width that is approximately equal to the width of bosses (42), or just slightly larger than the width of bosses (42), such that there is little to no rotational play between bending instrument (100) and rotational knob (40) when bending instrument (100) is mounted to dilation instrument (10). It should therefore be understood that engagement between rotational grounding features (140) and bosses (42) will prevent bending instrument (100) from rotating relative to rotary knob (40) when bending instrument (100) is mounted to dilation instrument (10). While rotary knob (40) is selectively rotatable relative to handle assembly (20) to re-orient malleable guide member (50), etc., the angular position of rotary knob (40) relative to handle assembly (20) will be fixed when actuator (160) is pivoted to bend malleable guide member (50). Thus, rotational grounding features (140) cooperate with bosses (42) to prevent bending instrument (100) from rotating relative to dilation instrument (10) as actuator (160) is pivoted to bend malleable guide member (50).

While FIG. 17 shows bending instrument (100) mounted to dilation instrument (10) while rotary knob (40) is oriented such that indicator fin (44) is located at the 9 o'clock position, it should also be understood that bending instrument (100) may be mounted to dilation instrument (10) while rotary knob (40) is oriented such that indicator fin (44) is located at the 3 o'clock position. In other words, rotational grounding features (140) and channel are configured to enable bending instrument (100) to fit on rotary knob (40) at two different angular positions that are 180° apart from each other.

In the present example, and as best seen in FIG. 19, forming channel (120) is defined by angled walls (122) that provide forming channel (120) with a v-shaped profile. This ensures that the malleable guide member (50) does not flatten and ovalize as malleable guide member (50) is pressed against walls (122) during the bending process. Malleable guide member (50) thus maintains a circular cross-sectional profile after being bent along forming channel (120). Other cross-sectional profiles (e.g., semi-circular cross-sectional profile, etc.) may also be used for channel (120) to support malleable guide member (50) and prevent malleable guide member (50) from flattening and ovalizing as malleable guide member (50) is pressed against walls (122) during the bending process. This ensures that malleable guide member (50) will allow guidewire (60) to slide freely through the inner lumen of malleable guide member (50); and dilation catheter (70) to slide freely along the exterior of malleable guide member (50) after malleable guide member (50) has been bent to achieve a desired bend angle.

Once the operator has pivoted actuator (160) to achieve the desired bend angle in malleable guide member (50), the operator may release actuator (160), thereby allowing actuator (160) to return to the position shown in FIGS. 6, 7A, 9A, 10A, and 11A. With malleable guide member (50) now in a bent configuration, the operator may decouple bending instrument (100) from dilation instrument (10) and pull malleable guide member (50) proximally out through opening (124). The operator may then use dilation instrument (10) in a dilation procedure as described in various references that are cited herein. Bending instrument (100) may simply be set aside during such dilation procedures.

III. EXEMPLARY INDICATORS ON BENDING INSTRUMENT

Figure 22:
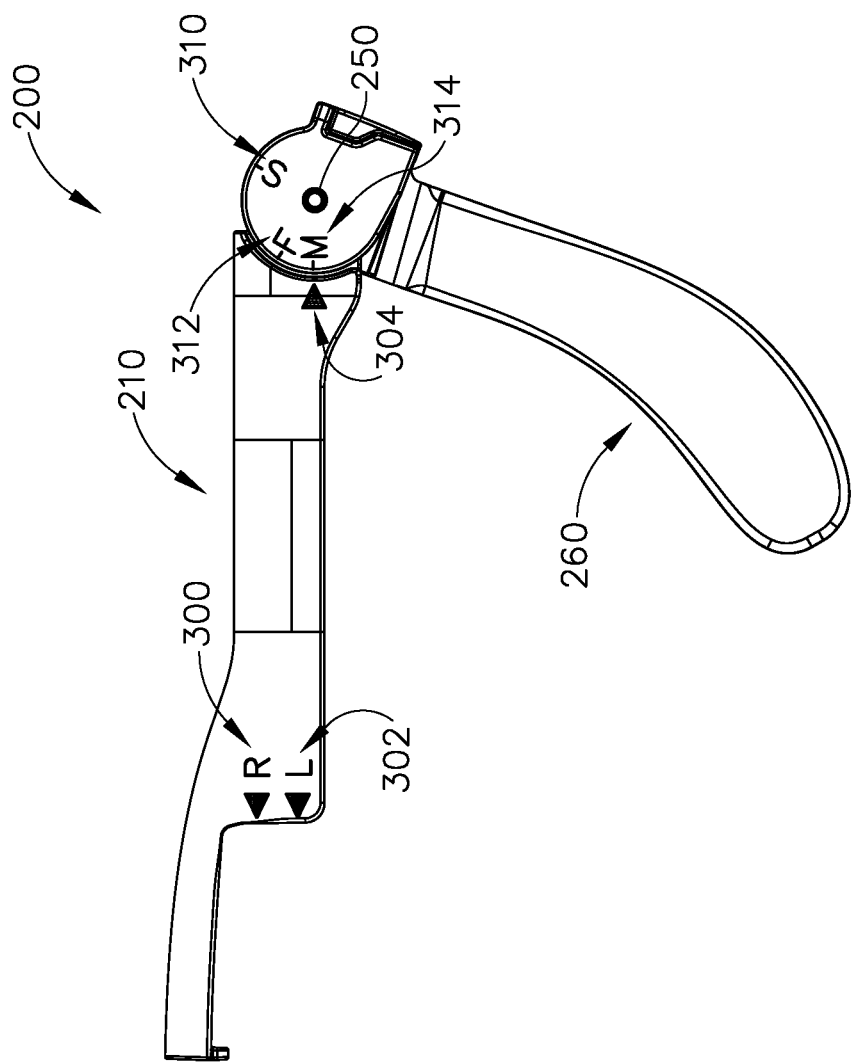
FIG. 22 depicts a side elevational view of the bending instrument of FIG. 6, with an actuator member in a third angular relationship with the grounding member of FIG. 12.

Those of ordinary skill in the art will recognize that access to different sinus ostia and/or other drainage passageways associated with the paranasal sinus may warrant bending malleable guide member (50) to different bend angles. While some operators may be able to readily discern the appropriate bend angle based on experience, it may be desirable to provide visual indicators that provide certainty and consistency in achieving particular bend angles based on the particular sinus ostium or other drainage passageway that is to be accessed. By way of example only, FIGS. 20-22 show an exemplary bending instrument (200) that is essentially a version of bending instrument (100) that has been modified to include bend indicators (304, 310, 312, 314). Other than including indicators (304, 310, 312, 314), bending instrument (200) of this example is configured and operable identically to bending instrument (100) described above. Indicators (304, 310, 312, 314) include a fixed indicator (304) that is located on grounding member (210) of instrument (200); and movable indicators (310, 312, 314) located on actuator (260) at certain angular positions about pin (250).

Fixed indicator (304) is in the form of an arrow pointing toward pin (250). Fixed indicator (304) is positioned to align with indicators (310, 312, 314) as actuator (260) is pivoted about pin (250), thereby providing a visual indication of the bend angle that will be achieved in malleable guide member (50) when actuator (260) is pivoted to the indicated position. In particular, in FIG. 20 shows fixed indicator (304) aligned with indicator (310), indicating that actuator (260) has been pivoted to a position where malleable guide member (50) will achieve the bend angle associated with indicator (310). FIG. 21 shows fixed indicator (304) aligned with indicator (312), indicating that actuator (260) has been pivoted to a position where malleable guide member (50) will achieve the bend angle associated with indicator (312). FIG. 22 shows fixed indicator (304) aligned with indicator (314), indicating that actuator (260) has been pivoted to a position where malleable guide member (50) will achieve the bend angle associated with indicator (314).

In the present example, indicator (310) is positioned at an angle associated with access to the sphenoid sinus. Indicator (310) is thus in the form of a short line with the letter "S" next to it, indicating its association with the sphenoid sinus. As shown, indicator (310) is located at an angular position corresponding to a 0° bend angle (i.e., straight) in malleable guide member (50). By way of example only, indicator (310) may be located at an angular position corresponding to a bend angle in malleable guide member (50) in the range of approximately 0° to 30°.

Also in the present example, indicator (312) is positioned at an angle associated with access to the frontal sinus. Indicator (312) is thus in the form of a short line with the letter "F" next to it, indicating its association with the frontal sinus. As shown, indicator (312) is located at an angular position corresponding to a 70° bend angle in malleable guide member (50). By way of further example only, indicator (312) may be located at an angular position corresponding to a bend angle in malleable guide member (50) in the range of approximately 50° to 90°.

Indicator (314) is positioned at an angle associated with access to the maxillary sinus. Indicator (314) is thus in the form of a short line with the letter "M" next to it, indicating its association with the maxillary sinus. As shown, indicator (314) is located at an angular position corresponding to a 90° bend angle in malleable guide member (50). By way of further example only, indicator (314) may be located at an angular position corresponding to a bend angle in malleable guide member (50) in the range of approximately 80° to 110°. It should also be understood that actuator (260) may be configured to engage a boss feature of grounding member (210), similar to a lateral projection (114) described above, when actuator (260) reaches the angular position associated with indicator (314). In other words, grounding member (210) may provide a hard stop that prevents actuator (260) from being pivoted further beyond the angular position associated with indicator (314).

In some instances, indicators (310, 312, 314) are positioned at angular locations that are just slightly beyond the angle at which malleable guide member (50) is sought to achieve. For instance, indicators (312) may be located just past approximately 70°; and indicators (314) may be located just past approximately 90°. This may account for a slight "spring back" effect that may be encountered in some versions of malleable guide member (50). For instance, if an operator wishes to achieve a bend angle of approximately 5° in malleable guide member (50), the operator may use bending instrument (200) to bend malleable guide member (50) to a bend angle of approximately 7°; and as soon as the operator releases actuator (260), the "spring back" effect may cause malleable guide member (50) ultimately achieve the desired bend angle of approximately 5°. Other suitable over-bending angles and their relationships with desired bend angles will be apparent to those of ordinary skill in the art in view of the teachings herein.

It should also be understood that bending instrument (200) may incorporate audible and/or tactile feedback features in addition to (or as an alternative to) the visual feedback features provided through indicators (304, 310, 312, 314). For instance, grounding member (210) may include a detent feature; and actuator (260) may include complementary detent features for each of the angular positions associated with indicators (310, 312, 314). Each detent feature of actuator (260) may engage the detent feature of grounding member (210) to provide audible and/or tactile feedback to the operator, further indicating that the angular positions associated with each indicators (310, 312, 314) has been achieved. For instance, when the operator pivots actuator (260) and hears/feels one "click" from the detent features, the operator will know that actuator (260) has been pivoted to the position corresponding to an angle associated with access to the sphenoid sinus. When the operator pivots actuator (260) and hears/feels two "clicks" from the detent features, the operator will know that actuator (260) has been pivoted to the position corresponding to an angle associated with access to the frontal sinus. When the operator pivots actuator (260) and hears/feels three "clicks" from the detent features, the operator will know that actuator (260) has been pivoted to the position corresponding to an angle associated with access to the maxillary sinus. Various suitable forms that such detent features may take will be apparent to those of ordinary skill in the art in view of the teachings herein.

As noted above, lateral projection (114) may also be relied on to provide tactile feedback, as a hard stop, indicating that the operator has pivoted actuator (260) to the position corresponding to an angle associated with access to the maxillary sinus. As also noted above, additional lateral projections (114) may be used to provide different hard stop locations, thereby providing tactile feedback at different bend angles. In some such versions, lateral projections (114) may be removable from grounding member (110), such that the operator may select and secure the appropriate lateral projection (114) to grounding member based on the anatomical passageway that the operator wishes to access with instrument (10).

Those of ordinary skill in the art will also recognize that the bend orientation of malleable guide member (50) may influence the ergonomics of instrument (10), particularly depending on whether the operator wishes to grasp instrument (10) with their right hand or left hand; and depending on whether the operator wishes to use rigid guide member (30), malleable guide member (50), guidewire (60), and dilation catheter (70) to access paranasal structures in the left side of the patient's head or the right side of the patient's head. For instance, if the operator wishes to grasp instrument (10) with their right hand, the operator may wish to stand on the patient's right-hand side and have sliders (64, 74) oriented toward the operator. If the operator wishes to grasp instrument (10) with their left hand, the operator may wish to stand on the patient's left-hand side and have sliders (64, 74) oriented toward the operator.

When malleable guide member (50) is in a bent configuration, since the angular orientation of malleable guide member (50) may be varied via knob (40), there is a potential for confusion and mis-orientation since the right-handed operator would be positioned at the patient's right side while the left-handed operator would be positioned at the patient's left side. To prevent such confusion and mis-orientation, bending instrument (200) and dilation instrument (400) include complementary indicators (300, 302, 322) to assist operators in properly positioning bending instrument (200) on dilation instrument (400) based on whether the operator is right-handed or left-handed.

Figure 23:
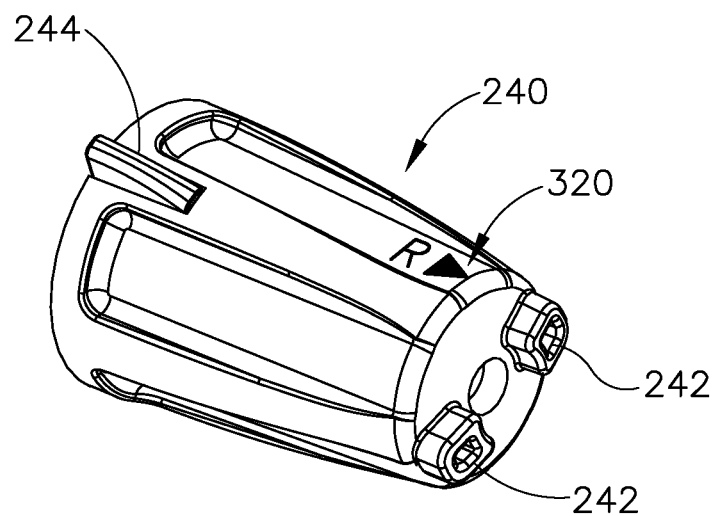
FIG. 23 depicts a perspective view of a rotary knob of the shaft assembly of FIG. 3.
Figure 24:
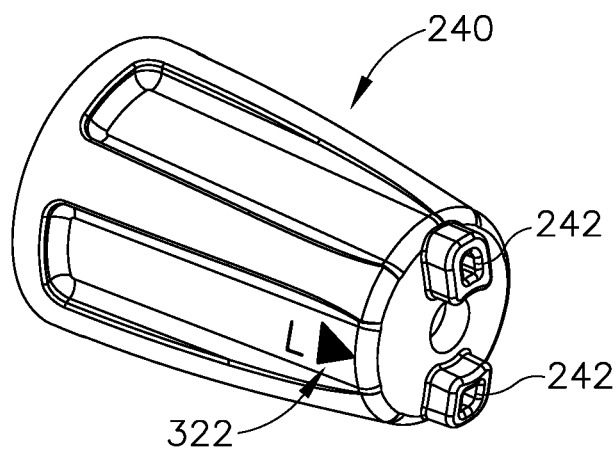
FIG. 24 depicts another perspective view of a rotary knob of the shaft assembly of FIG. 3.

Dilation instrument (400) of the present example is configured and operable just like dilation instrument (10) described above, except that dilation instrument of this example has a modified rotary knob (240). As shown in FIGS. 23-24, rotary knob (240) is substantially identical to rotary knob (40) in that rotary knob (240) includes a pair of distally projecting bosses (242) and a laterally projecting indicator fin (244). However, rotary knob (240) also includes a right-handed indicator (320) and a left-handed indicator (322). Right-handed indicator (320) comprises an arrow with the letter "R" next to it. Left-handed indicator (322) comprises an arrow with the letter "L" next to it. Indicators (320, 322) are angularly offset from each other by 180°. In some versions, handle assembly (420) of dilation instrument (400) also includes markings such as the letters "F" and "M" (not shown in present drawings). For instance, the "F" marking may be located at the 12 o'clock position; one "M" marking may be located at a 3 o'clock position; and the other "M" marking may be located at a 9 o'clock position. In such versions, it is understood that the operator will align indicator fin (244) with the "F" marking when accessing a frontal recess; and with one of the two "M" markings when accessing a maxillary sinus.

Bending instrument (200) also includes a right-handed indicator (300) and a left-handed indicator (302). Right-handed indicator (300) comprises an arrow with the letter "R" next to it. Left-handed indicator (302) comprises an arrow with the letter "L" next to it. In use, a right-handed operator may mount bending instrument (200) such that indicators (300, 320) align with each other; and a left-handed operator may mount bending instrument (200) to dilation instrument (400) such that indicators (302, 322) align with each other. It should be understood that the resulting alignment will be appropriate regardless of the angular orientation of rotary knob (240) at the time bending instrument (200) is mounted to dilation instrument (400). It should also be understood that bosses (242) will only permit bending instrument (200) to mount to dilation instrument (400) at two different angular orientations—one orientation in which indicators (300, 320) are aligned with each other and another orientation in which indicators (302, 322) are aligned with each other.

Figure 25:
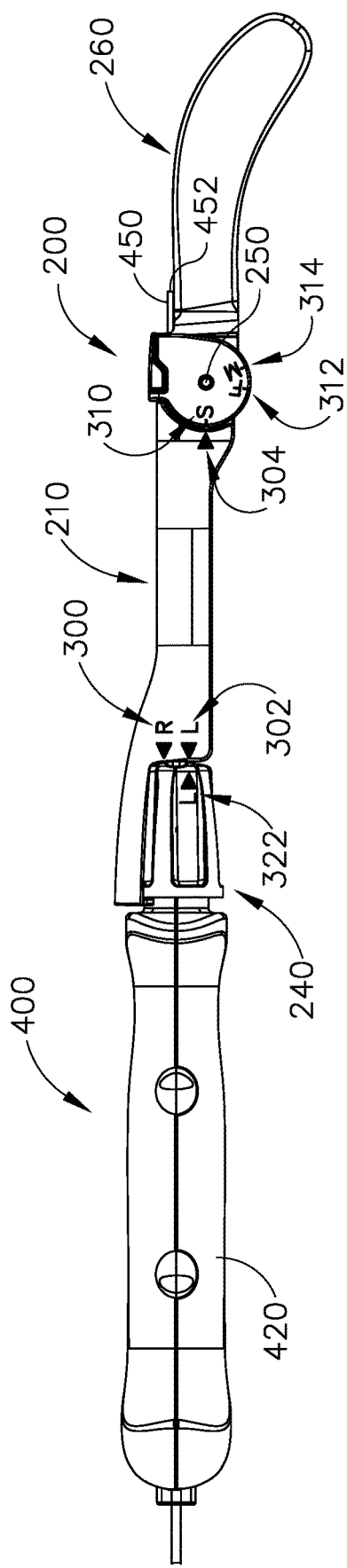
FIG. 25 depicts a bottom plan view of the bending instrument of FIG. 6 coupled with the dilation instrument of FIG. 1A, with the bending instrument at a first angular position about the axis of the shaft assembly.

As shown in FIG. 25, left-handed indicators (302, 322) are configured to align with each other when bending instrument (200) is coupled with dilation instrument (400) at an orientation suited for use by a left-handed operator. FIG. 25 shows bending instrument (200) coupled with dilation instrument (400) when rotary knob (240) is oriented such that indicator fin (244) is at the 12 o'clock position. It should be understood that pivoting actuator (260) will result in the malleable guide member (450) of dilation instrument (400) being bent along a plane that is transverse to the orientation of indicator fin (244). In particular, the distal end (452) of the bent malleable guide member (450) will be angularly offset from indicator fin (244) by 90° in the clockwise direction (viewing instrument (400) from the distal end toward the proximal end).

Figure 26:
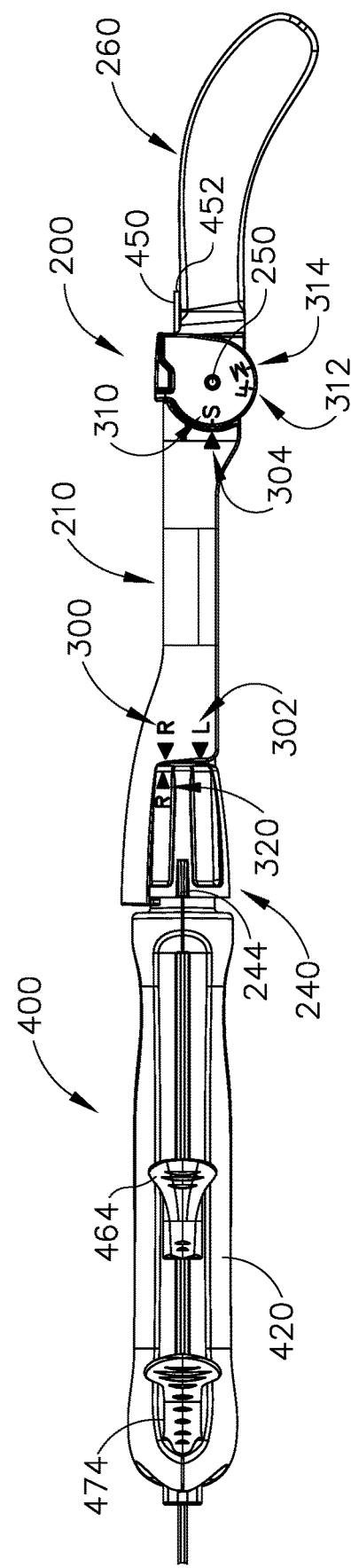
FIG. 26 depicts a top plan view of the bending instrument of FIG. 6 coupled with the dilation instrument of FIG. 1A, with the bending instrument at a second angular position about the axis of the shaft assembly.

As shown in FIG. 26, right-handed indicators (302, 320) are configured to align with each other with each other when bending instrument (200) is coupled with dilation instrument (400) at an orientation suited for use by a right-handed operator. FIG. 26 shows bending instrument (200) coupled with dilation instrument (400) when rotary knob (240) is oriented such that indicator fin (244) is at the 12 o'clock position. It should be understood that pivoting actuator (260) will result in the malleable guide member (450) of dilation instrument (400) being bent along a plane that is transverse to the orientation of indicator fin (244). In particular, the distal end (452) of the bent malleable guide member (450) will be angularly offset from indicator fin (244) by 90° in the counter-clockwise direction (viewing instrument (400) from the distal end toward the proximal end). It should be understood that this angular offset between distal end (452) and indicator fin (244) is 180° apart from the angular offset between distal end (452) and indicator fin (244) provided by mounting bending instrument (200) to dilation instrument (400) in the left-handed use configuration shown in FIG. 25.

If the operator wishes to access a patient's sphenoid sinus, malleable guide member (450) may be in a substantially straight configuration, such that the angular position of knob (240) will not matter. In other words, the angular position of knob (240) does not need to be adjusted for access to the patient's sphenoid sinus in the present example, regardless of whether the operator is grasping instrument (400) with their left hand or right hand; and regardless of whether the operator wishes to access the left sphenoid sinus of the patient or the right sphenoid sinus of the patient. In versions where malleable guide member (250) is bent (e.g., at an angle up to approximately 30°) to access a patient's sphenoid sinus, then the operator may orient knob (240) as described below with respect to accessing the patient's maxillary sinus.

If the operator wishes to access a patient's frontal recess, malleable guide member (450) would be pointing upwardly as sliders (464, 474) are pointing toward the operator, regardless of which hand the operator is grasping instrument (400) with. If the left-handed operator properly aligned left-handed indicators (302, 322) when the operator actuated bending instrument (400) to bend malleable guide member (450) to the frontal recess access angle, the bent malleable guide member (450) should be pointing upwardly (at a 3 o'clock orientation relative to handle assembly (420)) as sliders (464, 474) are pointing toward the operator with knob (240) at the 12 o'clock position. If the right-handed operator properly aligned right-handed indicators (300, 320) when the operator actuated bending instrument (400) to bend malleable guide member (450) to the frontal recess access angle, the bent malleable guide member (450) should be pointing upwardly (at a 9 o'clock orientation relative to handle assembly (420)) as sliders (464, 474) are pointing toward the operator with knob (240) at the 12 o'clock position. These orientations would be the same regardless of whether the operator is accessing the patient's left frontal recess or the patient's right frontal recess.

If the operator wishes to access a patient's right maxillary sinus, rotary knob (240) may be rotated 90° from the angular orientation associated with frontal recess access, to an angular orientation where bent malleable guide member (450) is pointing toward the patient's right side as sliders (464, 474) are pointing toward the operator, regardless of which hand the operator is grasping instrument (400) with. If the operator wishes to access a patient's left maxillary sinus, rotary knob (240) may be rotated 90° from the angular orientation associated with frontal recess access, to an angular orientation where bent malleable guide member (450) is pointing toward the patient's left side as sliders (464, 474) are pointing toward the operator, regardless of which hand the operator is grasping instrument (400) with.

Thus, a left-handed operator may rotate rotary knob (240) to the 9 o'clock position, thereby orienting bent malleable guide member (450) at the 12 o'clock position, to access the patient's left maxillary sinus. The left-handed operator may rotate rotary knob (240) to the 3 o'clock position, thereby orienting bent malleable guide member (450) at the 6 o'clock position, to access the patient's right maxillary sinus. A right-handed operator may rotate rotary knob (240) to the 9 o'clock position, thereby orienting bent malleable guide member (450) at the 6 o'clock position, to access the patient's left maxillary sinus. The right-handed operator may rotate rotary knob (240) to the 3 o'clock, thereby orienting bent malleable guide member (450) at the 12 o'clock position, to access the patient's right maxillary sinus.

IV. EXEMPLARY UNBENDING INSTRUMENT

Figure 27:
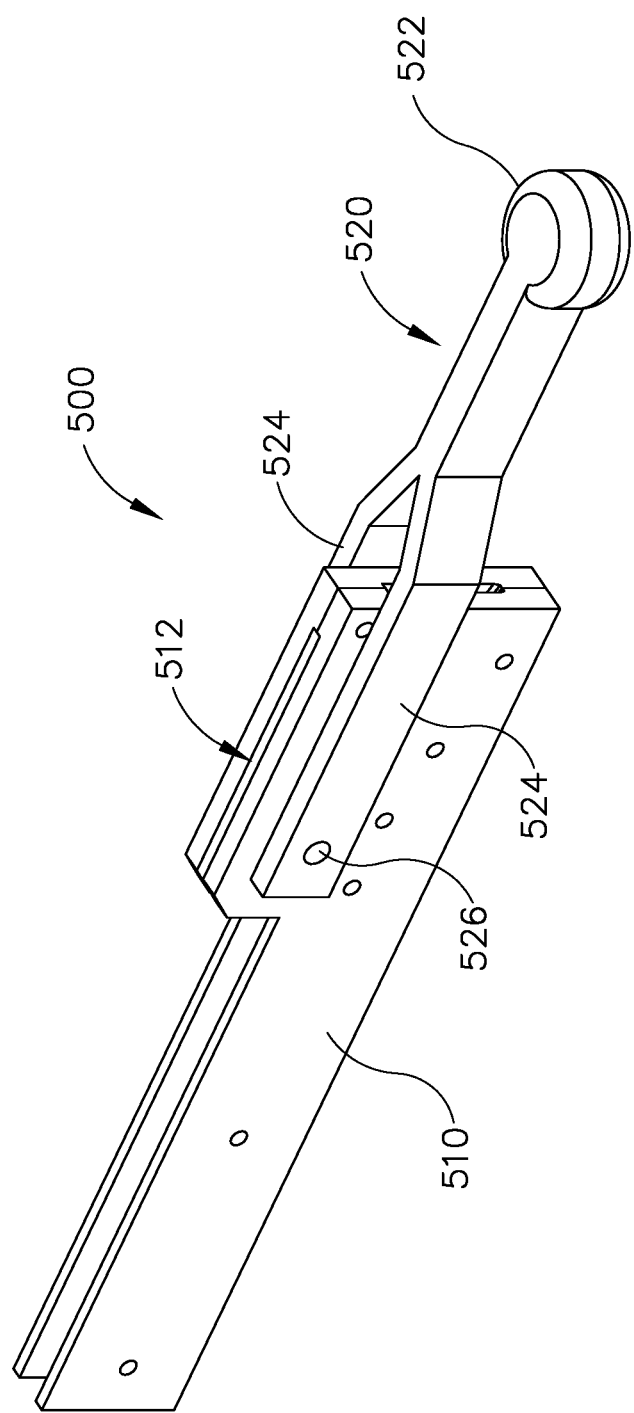
FIG. 27 depicts a perspective view of an exemplary unbending instrument.
Figure 28A:
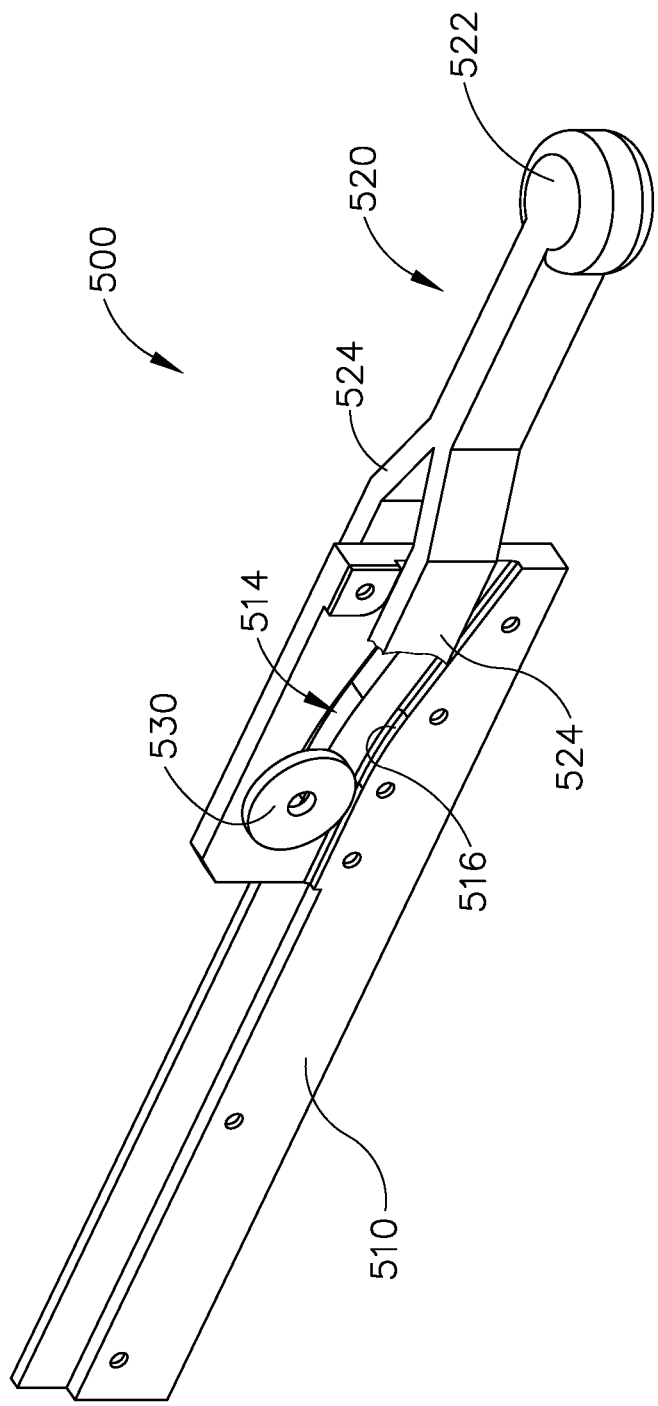
FIG. 28A depicts a perspective view of the unbending instrument of FIG. 27, with a portion of the instrument broken away to reveal internal details, and with a roller element in a proximal position.

As noted above, malleable guide member (50) may be configured such that unbending or re-bending malleable guide member (50) is not easy without the assistance of another instrument. While bending instrument (100, 200) is capable of bending malleable guide member (50) in one direction, bending instrument (100, 200) is not capable of un-bending malleable guide member (50) in the opposite direction (e.g., to achieve a straight configuration or otherwise less bent configuration). FIGS. 27-28C show one exemplary unbending instrument (500) that may be used to un-bend a bent malleable guide member (50). By way of example only, unbending instrument (500) may be used to un-bend a malleable guide member (50) that had previously been bent by bending instrument (100, 200). Alternatively, unbending instrument (500) may be used to un-bend a malleable guide member (50) that had previously been bent by some other instrument.

Unbending instrument (500) of this example comprises a body (510) defining a channel (512). Body (510) further defines a slot (514) and an unbending surface (516). An actuator (520) is movably coupled with body (510). Actuator (520) comprises a grip (522) and a pair of prongs (524). A wheel (530) is positioned in channel (512) of body (510) and is coupled with prongs (524) by an axle (526). Axle (526) passes through slot (514) of body (510). Actuator (520) is operable to pull wheel (530) via axle (526), and slot (514) is operable to guide movement of wheel (530) via axle (526) as actuator (520) pulls wheel (530) trough body (510).

Figure 28B:
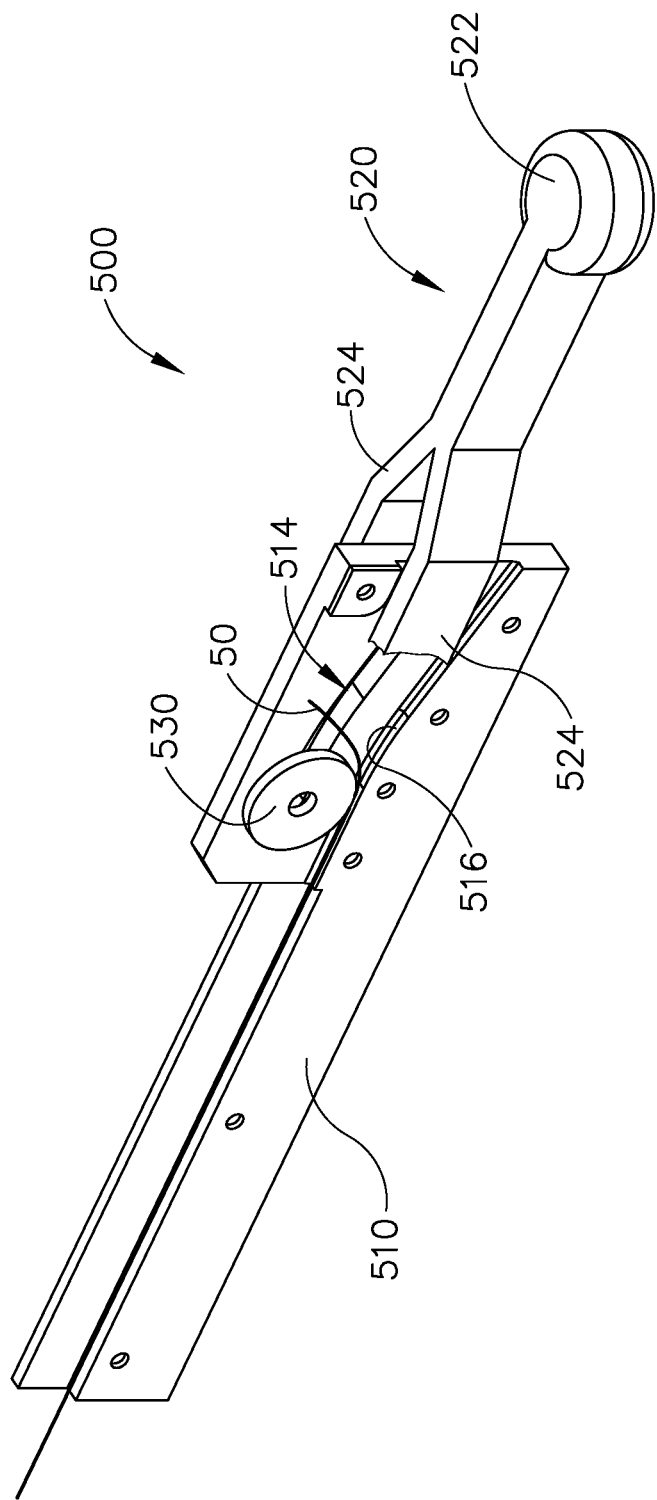
FIG. 28B depicts a perspective view of the unbending instrument of FIG. 27, with a portion of the instrument broken away to reveal internal details, and with a malleable member positioned in the unbending instrument.
Figure 28C:
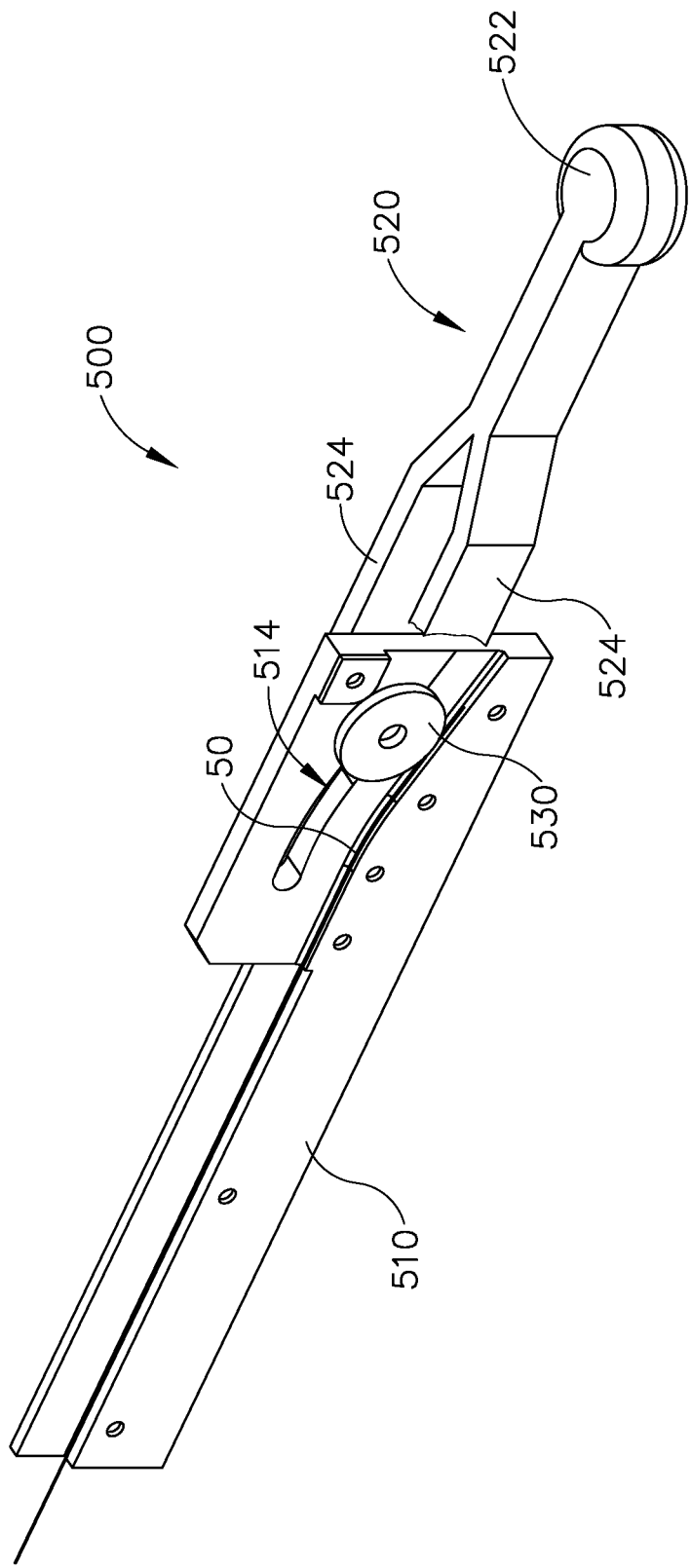
FIG. 28C depicts a perspective view of the unbending instrument of FIG. 27, with a portion of the instrument broken away to reveal internal details, and with the roller element in a distal position.

As shown in FIG. 28B, an operator may insert the bent distal end of malleable guide member (50) into body (510) to position malleable guide member (50) between wheel (530) and unbending surface (516). While holding malleable guide member (50) stationary relative to body (510), the operator may then pull actuator (520) to drive wheel (530) along malleable guide member (50) to the position shown in FIG. 28C. As wheel (530) traverses malleable guide member (50), wheel (530) and unbending surface (516) cooperate to unbend malleable guide member (50) as shown. In the present example, unbending surface (516) is inclined to over-bend malleable guide member (50), under the assumption that the material properties of malleable guide member (50) may provide some degree of slight "spring back" as noted above. After reaching the stage shown in FIG. 28C, the operator may pull malleable guide member (50) from body (510). At this stage, malleable guide member (50) will be substantially straight and may thus be re-used or re-bent as desired.

While FIGS. 28B-28C show only malleable guide member (50), it should be understood that unbending instrument (500) may be configured to accommodate other features of dilation instrument (10). In other words, it is not necessary to remove malleable guide member (50) from dilation instrument (10) in order to use unbending instrument (500) to unbend malleable guide member (50).

Figure 29:
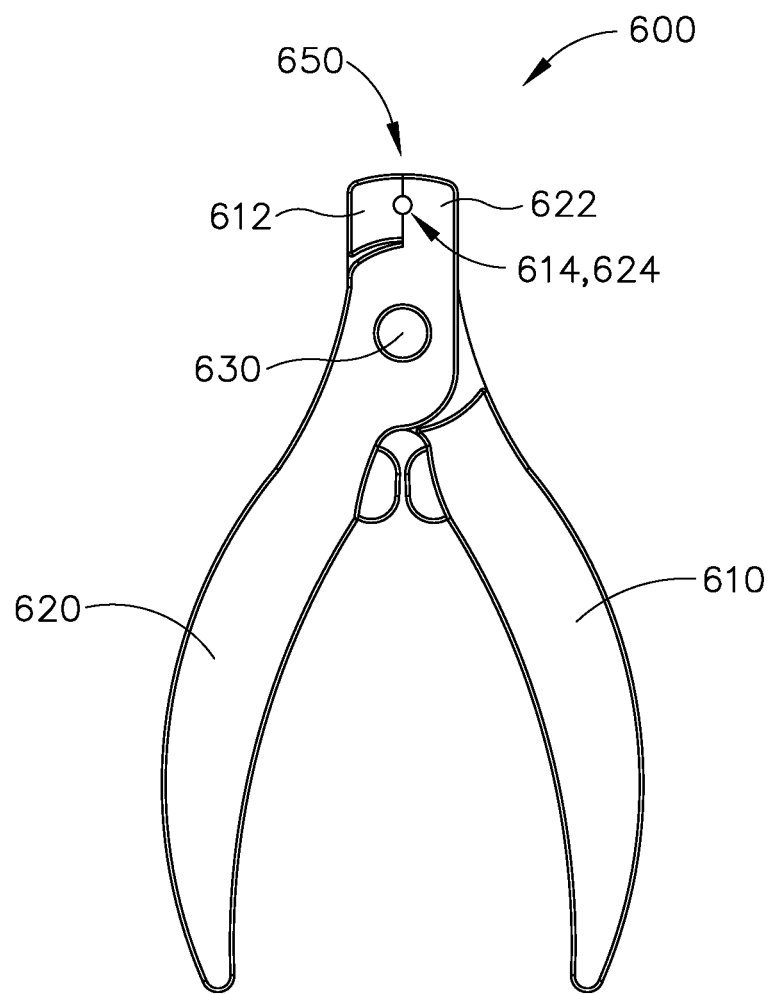
FIG. 29 depicts a side elevational view of another exemplary unbending instrument.
Figure 30:
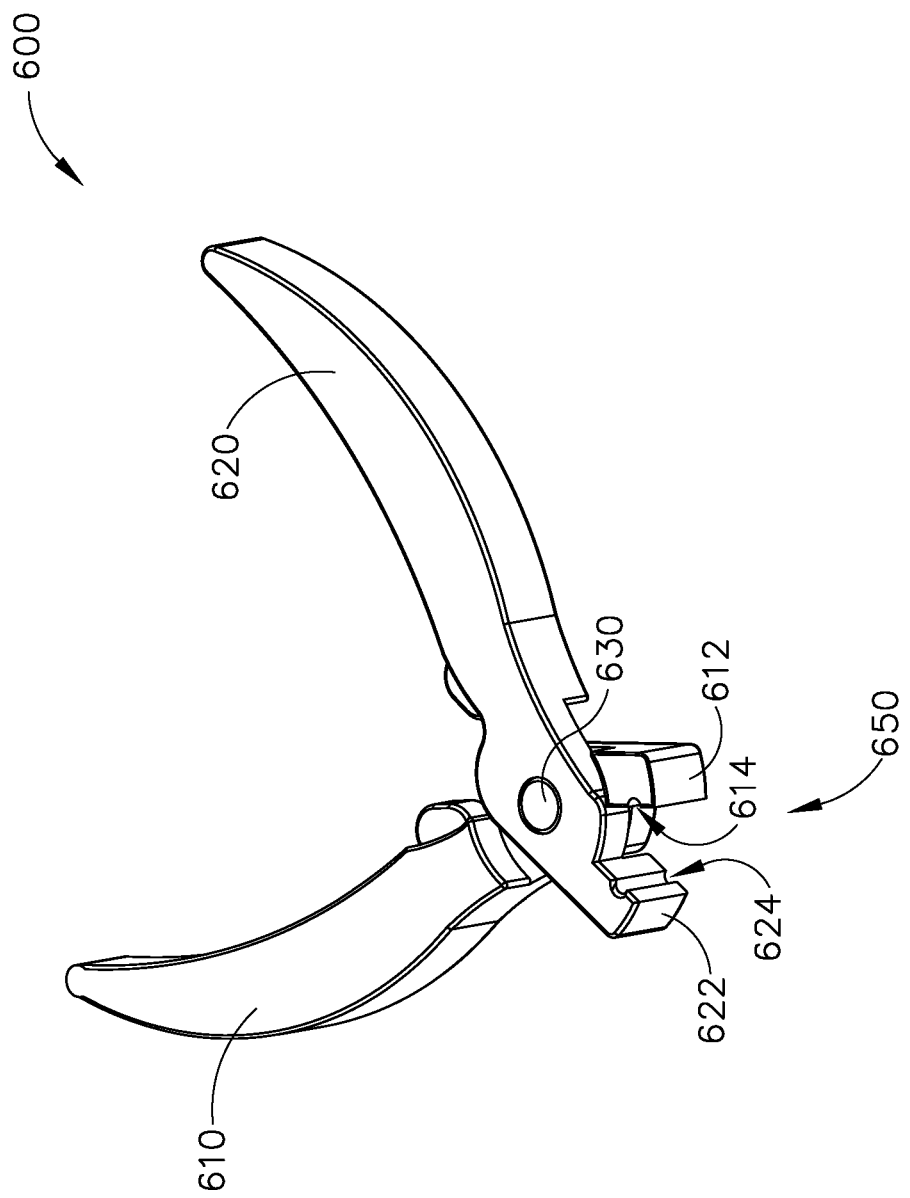
FIG. 30 depicts a perspective view of the distal end of the unbending instrument of FIG. 29.

FIGS. 29-30 show another exemplary unbending instrument (600) that may be used to un-bend a bent malleable guide member (50). By way of example only, unbending instrument (600) may be used to un-bend a malleable guide member (50) that had previously been bent by bending instrument (100, 200). Alternatively, unbending instrument (600) may be used to un-bend a malleable guide member (50) that had previously been bent by some other instrument. Unbending Instrument (600) of this example comprises a pair of arms (610, 620) that are coupled together via a pivot (630). The distal ends (612, 622) cooperate to form an end effector (650) that may be used to grasp and unbend malleable guide member (50). Each distal end (612, 622) defines a respective channel (614, 624). Channels (614, 624) are sized and configured to receive and grip malleable guide member (50) when end effector (650) is closed upon malleable guide member (50). Channels (614, 624) may each have a cross-sectional profile that is semi-circular, v-shaped, or otherwise shaped.

In use, an operator may grasp malleable guide member (50) with end effector (650), unbend a portion of malleable guide member (50) by clamping arms (610, 620) and twisting to straighten malleable guide member (50), release that portion of malleable guide member (50), grasp another portion of guide member (50) with end effector (650), unbend that portion of malleable guide member (50) by manipulating arms (610, 620), and so on until the operator has sufficiently unbent malleable guide member (50). Unbending instrument (600) may also be operable to bend malleable guide member (50) into different custom shapes. In some such versions, the edges of channels (614, 624) may be rounded to prevent formation of kinks in malleable guide member (50) as end effector (650) is used to bend or unbend malleable guide member (50). Various other suitable ways in which unbending instrument (600) may be used will be apparent to those of ordinary skill in the art in view of the teachings herein.

V. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a grounding member, wherein the grounding member comprises: (i) a first grounding feature, wherein the first grounding feature is configured to engage a dilation instrument, and (ii) a bending channel, wherein the bending channel is configured to receive a malleable member of the dilation instrument; and (b) an actuator, wherein the actuator is pivotably coupled with the grounding member, wherein the actuator comprises a bearing surface, wherein the bearing surface is configured to cooperate with the bending channel to thereby bend the malleable member of the dilation instrument as the actuator is pivoted relative to the grounding member.

Example 2

The apparatus of Example 1, wherein the first grounding feature is configured to provide longitudinal alignment between the grounding member and the dilation instrument.

Example 3

The apparatus of Example 2, further comprising a second grounding feature, wherein the second grounding feature is configured to provide angular alignment between the grounding member and the dilation instrument.

Example 4

The apparatus of any one or more of Examples 1 through 3, wherein the first grounding feature is configured to prevent longitudinal movement of the grounding member relative to the dilation instrument.

Example 5

The apparatus of Example 4, wherein the first grounding feature comprises a ridge.

Example 6

The apparatus of Example 5, wherein the dilation instrument comprises a proximally facing surface, wherein the ridge is configured to engage the proximally facing surface.

Example 7

The apparatus of any one or more of Examples 4 through 6, further comprising a second grounding feature, wherein the second grounding feature is configured to prevent rotation of the grounding member relative to the dilation instrument.

Example 8

The apparatus of Example 1, wherein the first grounding feature is configured to provide angular alignment between the grounding member and the dilation instrument.

Example 9

The apparatus of Example 1 or Example 8, wherein the first grounding feature is configured to prevent rotation of the grounding member relative to the dilation instrument.

Example 10

The apparatus of Example 9, wherein the dilation instrument comprises at least one distally projecting boss feature, wherein the first grounding feature is configured to engage the at least one distally projecting boss feature.

Example 11

The apparatus of any one or more of Examples 9 through 10, wherein the first grounding feature comprises at least one laterally projecting flange.

Example 12

The apparatus of any one or more of Examples 1 through 11, wherein the actuator is configured to pivot from a non-pivoted position to at least one pivoted position, wherein the actuator is configured to substantially align with the grounding member when the actuator is in the non-pivoted position.

Example 13

The apparatus of any one or more of Examples 1 through 12, further comprising a resilient member, wherein the actuator is configured to pivot from a non-pivoted position to at least one pivoted position, wherein the resilient member is configured to bias the actuator toward the non-pivoted position.

Example 14

The apparatus of any one or more of Examples 1 through 13, wherein the bending channel has a v-shaped cross-sectional profile.

Example 15

The apparatus of any one or more of Examples 1 through 14, wherein the bending channel extends along a curve.

Example 16

The apparatus of any one or more of Examples 1 through 15, wherein the grounding member has an indicator, wherein the actuator has an indicator, wherein the indicator of the actuator is configured to align with the indicator of the grounding member to visually indicate a predefined bend angle.

Example 17

The apparatus of any one or more of Examples 1 through 16, wherein the dilation instrument is configured for use in a selected one of a right-handed configuration or a left-handed configuration, wherein the grounding member has a right-handed indicator and a left-handed indicator, wherein the right-handed indicator is configured to align with a corresponding indicator on the dilation instrument to indicate use in the right-handed configuration, wherein the left-handed indicator is configured to align with a corresponding indicator on the dilation instrument to indicate use in the left-handed configuration.

Example 18

The apparatus of any one or more of Examples 1 through 17, wherein the grounding member comprises a laterally projecting boss, wherein the laterally projecting boss is configured to restrict pivotal movement of the actuator relative to the grounding member.

Example 19

A system comprising: (a) a bending instrument, wherein the bending instrument comprises: (i) a grounding member, wherein the grounding member comprises: (A) a first grounding feature, and (B) a bending channel, and (ii) an actuator, wherein the actuator is pivotably coupled with the grounding member, wherein the actuator comprises a bearing surface; and (b) a dilation instrument, wherein the dilation instrument comprises: (i) a malleable guide member, and (ii) a second grounding feature, wherein the second grounding feature is proximal to the malleable guide member; wherein the first grounding feature is configured to engage the second grounding feature to prevent longitudinal movement or rotation of the grounding member relative to the dilation instrument; wherein the bending channel is configured to receive the malleable guide member of the dilation instrument; wherein the bearing surface is configured to cooperate with the bending channel to thereby bend the malleable member as the actuator is pivoted relative to the grounding member.

Example 20

A method of configuring a dilation instrument, the method comprising: (a) positioning a malleable guide member of the dilation instrument in a bending channel of a bending instrument, wherein the bending instrument comprises a grounding member and an actuator; (b) engaging a grounding feature of the grounding member with a grounding feature of the dilation instrument, thereby preventing longitudinal movement or rotation of the grounding member relative to the dilation instrument; (c) pivoting the actuator relative to the grounding member, thereby driving a bearing surface of the grounding member against the malleable guide member to thereby bend a portion of the malleable guide member along the bending channel; and (d) removing the malleable guide member from the bending channel, wherein the malleable guide member is in a bent state when the malleable guide member is removed from the bending channel.

VI. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system comprising:
 (a) a bending instrument, wherein the bending instrument comprises:
  a grounding member, wherein the grounding member comprises:
   (A) a first grounding feature, and
   (B) a bending channel, and
  (ii) an actuator, wherein the actuator is pivotably coupled with the grounding member, wherein the actuator comprises a bearing surface; and
 (b) a dilation instrument, wherein the dilation instrument comprises:
  (i) a malleable guide member, and
  (ii) a second grounding feature, wherein the second grounding feature is proximal to the malleable guide member;
 wherein the first grounding feature is configured to engage the second grounding feature to prevent longitudinal movement or rotation of the grounding member relative to the dilation instrument;
 wherein the bending channel is configured to receive the malleable guide member of the dilation instrument;
 wherein the bearing surface is configured to cooperate with the bending channel to thereby bend the malleable member as the actuator is pivoted relative to the grounding member.

2. The system of claim 1, wherein the actuator is configured to pivot from a a non-pivoted position to at least one pivoted position, wherein the actuator is configured to substantially align with the grounding member in the non-pivoted position, and a second angular position relative to the grounding member to thereby bend the malleable member.

3. The system of claim 1, wherein the bending instrument further comprises a resilient member disposed between the actuator and the grounding member, wherein the resilient member is configured to bias the actuator to a non-pivoted position relative to the grounding member.

4. The system of claim 1, wherein the first grounding feature comprises at least one laterally projecting flange.

5. The system of claim 4, wherein the at least one laterally projecting flange defines a channel.

6. The system of claim 5, wherein the second grounding feature of the dilation instrument comprises at least one distally projecting boss feature, wherein the at least one distally projecting boss feature is configured to mate with the channel to prevent rotational movement of the grounding member relative to the dilation instrument.

7. The system of claim 6, wherein the first grounding feature is configured to mate with the second grounding feature at two distinct angular alignments relative to each other.

8. The system of claim 7, wherein the two distinct angular alignments further comprise a right-handed orientation and a left-handed orientation.

9. The system of claim 6, wherein the first grounding feature comprises a first pair of indicators, wherein the second grounding feature comprises a second set of indicators, wherein the first pair of indicators and the second pair of indicator are configured to indicate whether the first grounding feature and the second grounding feature are mated in the right-handed orientation or the left-handed orientation.

10. The system of claim 1, wherein the bending channel comprises a v-shaped cross-sectional profile.

11. The system of claim 1, wherein the malleable guide member is hollow.

12. The system of claim 1, wherein the bending channel extends along a curve.

13. The system of claim 1 wherein the first grounding feature comprises a laterally projecting boss, wherein the laterally projecting boss is configured to restrict pivotal movement of the actuator relative to the grounding member.

14. The system of claim 1, wherein the first grounding feature comprises a ridge.

15. The system of claim 1, wherein the second grounding feature comprises a proximally facing surface, wherein the ridge is configured to engage the proximally facing surface to prevent longitudinal movement of the grounding member relative to the second grounding feature.

* * * * *